(12) United States Patent
Cohen et al.

(10) Patent No.: US 9,493,834 B2
(45) Date of Patent: Nov. 15, 2016

(54) METHOD FOR DETECTING A PANEL OF BIOMARKERS

(75) Inventors: Daniel Cohen, Le Vésinet (FR); Ilya Chumakov, Vaux le Penil (FR); Serguei Nabirochkin, Chatenay Malabry (FR); Oxana Guerassimenko, Milly-la-Forêt (FR); Esther Graudens, Paris (FR)

(73) Assignee: PHARNEXT, Issy les Moulineaux (FR)

( * ) Notice: Subject to any disclaimer, the term of this patent is extended or adjusted under 35 U.S.C. 154(b) by 0 days.

(21) Appl. No.: 13/387,174

(22) PCT Filed: Jul. 29, 2010

(86) PCT No.: PCT/EP2010/061020
§ 371 (c)(1),
(2), (4) Date: Jul. 9, 2012

(87) PCT Pub. No.: WO2011/012672
PCT Pub. Date: Feb. 3, 2011

(65) Prior Publication Data
US 2012/0283114 A1 Nov. 8, 2012

Related U.S. Application Data

(60) Provisional application No. 61/229,356, filed on Jul. 29, 2009.

(51) Int. Cl.
*G01N 33/53* (2006.01)
*C12Q 1/68* (2006.01)
*G01N 33/68* (2006.01)

(52) U.S. Cl.
CPC ......... *C12Q 1/6883* (2013.01); *G01N 33/6896* (2013.01); *C12Q 2600/156* (2013.01); *C12Q 2600/158* (2013.01); *G01N 2800/2821* (2013.01); *G01N 2800/60* (2013.01)

(58) Field of Classification Search
None
See application file for complete search history.

(56) References Cited

U.S. PATENT DOCUMENTS

2007/0082350 A1* 4/2007 Landfield et al. ................ 435/6

FOREIGN PATENT DOCUMENTS

EP 1774972 4/2007

OTHER PUBLICATIONS

Ray, S. et al. "Classification and prediction of clinical Alzheimer's diagnosis based on plasma signaling proteins" *Nature Medicine*, Nov. 1, 2007, pp. 1359-1362, vol. 13, No. 11.
Schipper, H. M. "The role of biologic markers in the diagnosis of Alzheimer's disease" *Alzheimer's & Dementia*, 2007, pp. 325-332, vol. 3, No. 4.
Britschgi, M. "Blood Protein Signature for the Early Diagnosis of Alzheimer Disease" *Achieves of Neurology*, Feb. 2009, pp. 161-165, vol. 66, No. 2.
Rogelj, B. et al. "The X11/Mint family of adaptor proteins" *Brain Research Reviews*, Sep. 1, 2006, pp. 305-315, vol. 52, No. 2.
Written Opinion in International Application No. PCT/EP2010/061020, Nov. 12, 2010, pp. 1-9.

* cited by examiner

*Primary Examiner* — Gregory S Emch
(74) *Attorney, Agent, or Firm* — Saliwanchik, Lloyd & Eisenschenk

(57) ABSTRACT

The present invention relates to development, validation and application of new sets of biomarkers for diagnosis of Alzheimer's disease (AD) and related disorders including early diagnosis of MCI and early prodrome of AD, identification of disease sub types, prediction of their response to disease management procedures, drugs and their combinations and for monitoring response for these treatments, including validation of biomarkers for clinical trials.

10 Claims, No Drawings

METHOD FOR DETECTING A PANEL OF BIOMARKERS

This application is the U.S. national stage application of International Patent Application No. PCT/EP2010/061020, filed Jul. 29, 2010, which claims the benefit of U.S. Provisional Patent Application No. 61/229,356, filed Jul. 29, 2009.

FIELD OF THE INVENTION

The present invention relates to development, validation and application of new sets of biomarkers for diagnosis of Alzheimer's disease (AD) and related disorders including early diagnosis of MCI and early prodrome of AD, identification of disease sub types, prediction of their response to disease management procedures, drugs and their combinations and for monitoring response for these treatment, including validation of biomarkers for clinical trials. In particular, the present invention relates to the field of detection and of monitoring treatment of neurodegenerative disorders, including Alzheimer's disease, prodrome condition of Alzheimer disease or mild cognitive impairment (MCI). More specifically, the present invention relates to proteinaceous, lipid, glucidic and metabolite biomarkers that can be measured in biological fluids, which can be used to aid in the detection, subclassification, prediction of drug treatment and follow up of this treatment of neurodegenerative disorders, including Alzheimer's disease, its prodrome and mild cognitive impairment.

BACKGROUND OF THE INVENTION

AD is at present the most common cause of dementia. It is clinically characterized by a global decline of cognitive function that progresses slowly and leaves end-stage patients bound to bed, incontinent and dependent on custodial care. Death occurs, on average, 9 years after diagnosis (Citron et al., 2004). The incidence rate of AD increases dramatically with age. United Nation population projections estimate that the number of people older than 80 years will approach 370 million by the year 2050. Currently, it is estimated that 50% of people older than age 85 years are afflicted with AD. Therefore, more than 100 million people worldwide will suffer from dementia in 50 years. The vast number of people requiring constant care and other services will severely affect medical, monetary and human resources (Suh & Checker, 2002).

Currently, clinical diagnosis of AD is based on structured interviews (patient histories), and neuropsychological examinations coupled with imaging or neurophysiological scans (CT, MRI, PET and/or SPECT scans and EEG) to rule out other explanations of memory loss including temporary (depression or vitamin B12 deficiency) or permanent conditions (stroke) and is based on NINCDS-ADRDA Work group criteria (McKhann et al., 1984) and the American Psychiatric Association Diagnostic and Statistical Manual of Mental Disorders (4th Ed. Washington D.C., Am Psychiatric Assoc., 1997).

Unfortunately, clinical diagnostic methods are not foolproof. Evidence based review of current literature shows clinical diagnostic accuracy of 65 to 90%. Higher accuracy rates are generally associated with specialized centers (memory disorder clinics) focused on memory disorders whereas lower rates are likely associated with primary care physicians. Additionally, accuracy of the clinical diagnosis is likely lower during early stages of the disease when symptoms are difficult to differentiate from normal age-associated cognitive decline. More recently, studies suggest that a condition termed mild cognitive impairment (MCI) represents prodromal AD and if diagnosed early represents the best opportunity for pharmaceutical intervention. The clinical criteria used for diagnosis of MCI are those of Petersen et al. (1999) and include: 1) memory complaints corroborated by an informant, 2) objective memory impairment for age and education, 3) normal general cognitive function, 4) intact activities of daily living, and 5) the subject does not meet criteria for dementia.

Further complicating diagnosis and treatment of AD is the lack of a reliable biomarker that specifically identifies AD subjects, particularly early in the prodromal stage of the disease (MCI). In view of the magnitude of the public health problem posed by AD, considerable research efforts have been undertaken to elucidate the etiology of AD as well as to identify biomarkers, characteristic proteins or metabolites objectively measured as an indicator of pathogenic processes, that can be used to diagnose and/or predict whether a person is likely to develop AD.

Most studies of biomarkers of AD have focused on measurement in the cerebrospinal fluid (CSF). Because of its intimate contact with the brain, pathogenic changes in the brain that result in alterations in proteins/peptides would likely be reflected in the CSF.

A number of U.S. patents and published applications relate to methods for diagnosing AD, including U.S. Pat. Nos. 4,728,605, 5,874,312, 6,027,896, 6,114,133, 6,130,048, 6,210,895, 6,358,681, 6,451,547, 6,461,831, 6,465,195, 6,475,161, 6,495,335, 2005/0244890, and 2005/0221348. Additionally, a number of reports in the scientific literature relate to certain biochemical markers and their correlation/association with AD, including Fahnestock et al., 2002; Masliah et al., 1995; Power et al., 2001; and Burbach et al., 2004. Additionally, Li et al. (2002) and Sanna et al. (2003) have investigated Leptin in relation to memory and multiple sclerosis, respectively.

Three different biomarkers in CSF have been particularly well documented: neuronal thread protein, tau (total; T-tau and various phosphorylated forms; P-tau) and derivatives of amyloid precursor protein (APP) including $A\beta_{40}$ and $A\beta_{42}$. Neuronal thread protein is described to be overexpressed in brain neurons in AD patients. A quantitative test for measuring levels of a specific type of neuronal thread protein (AD7c-NTP) in CSF and urine has been developed. Quite a number of studies have evaluated CSF-tau as an antemortem marker for AD mainly using enzyme-linked immunoabsorbent assays (ELISA) as the measurement assay. In past studies, total tau (T-tau) has been measured although there is an increasing body of literature also describing the analysis of phosphorylated (P-tau) variants of the same protein involved in the formation of neurofibrillary tangles. ELISAs that can distinguish between the major form of Aβ ending at amino acid 40 ($A\beta_{40}$) and the senile plaque forming species ending at position 42 ($A\beta_{42}$) have also been developed and evaluated extensively for CSF analysis. These three assays, either used individually, or in the case of tau and $A\beta_{42}$, in combination, have not demonstrated the required sensitivity and specificity values for routine clinical use, particularly for early diagnosis and discrimination between AD and other non-AD dementias. In addition, attempts to measure tau and $A\beta_{42}$ in blood have been met with limited success, further restricting their widespread adoption into clinical practice.

A wide spectrum of other aberrations, other than NTP, Tau and Aβ, has been reported in AD patient CSF. Many of the identified (protein sequence confirmed) CSF markers reported herein have been shown to be either increased or decreased in AD patients versus normal individuals. For example, the protein Ubiquitin is known to complex with hyperphosphorylated Tau during maturation of NFTs in the brains of AD patients (Iqbal et al., 1998). Ubiquitin levels in CSF of AD and neurological control groups have been shown to be significantly higher than those of non-neurological aged controls (Wang et. al., 1991; Kudo et al., 1994).

The acute phase/inflammatory protein alpha(1)-antichymotrypsin (ACT) is overproduced in the AD brain. ACT also can promote the formation of, and is associated with, neurotoxic amyloid deposits (Potter et al., 2001). The levels of ACT in both serum and CSF are significantly and specifically higher in patients with Alzheimer-type dementia than in control subjects (Matsubara et al., 1990). There is a particularly close association of increases in CSF-ACT with late onset AD (Harigaya et al., 1995).

Chromogranin A (CrA) is the major protein of large dense-core synaptic vesicles and may be of value as a biochemical marker for synaptic function in AD. One report described no difference between AD, vascular dementia, and age-matched control groups except when comparing a familial subtype (AD Type I) with controls where there was a statistically significant elevation of CSF CrA in the diseased individuals (Blennow et al., 1995).

Beta-2-Microglobulin (β2M) is an initiator of inflammatory responses modulated by interferons and certain cytokines (Hoekman et al., 1985). A proteome analysis of CSF by two-dimensional electrophoresis (2D-gel) has shown a significant increase of β2M in AD patients (Davidsson et al., 2002), and more recently these results were confirmed by SELDI analysis (Carrette et al, 2003).

Transthyretin (TTR) has been shown to interact with A.β, possibly preventing amyloid formation in biological fluids and in the brain. (Tsuzuki et al., 2000). One identified TTR isoform was shown to be increased in AD-CSF using 2D gel analysis of a small number of AD and control patients (Davidsson, supra.). However, this result conflicts with other reports showing a clear decrease of TTR in CSF from AD patients compared with controls (Serot et al., 1997; Riisoen et al., 1998). This decrease is also negatively correlated with the senile plaque (SP) abundance (Merched et al., 1998).

Cystatin C, a cysteine protease inhibitor, has been implicated in the neurodegenerative and repair processes of the nervous system, and the deposition of the same protein together with beta amyloid peptide was found as cerebral amyloid angiopathy (CAA) in different types of dementias (Levy et al., 2001). Full length Cystatin C was found as a CSF marker for AD in a previous SELDI profiling study (Carrette, supra.). A relative blood-brain barrier (BBB) dysfunction is associated with AD among very elderly individuals. The CSF/serum albumin ratio can be used as a measure of BBB function. Mean CSF/serum albumin ratio has been reported to be higher in all dementias studied, including AD, than in nondemented individuals (Skoog et al., 1998).

Transferrin (TF) plays a role in anti-oxidant defense in serum and is also produced in the brain where its role in oxidative stress is unclear. A study on Down's syndrome patients suffering from progressive dementia showed decreased levels of TF when compared to age-matched controls with no neurological disease (Elovaara, 1984).

Prostaglandin-D-Synthase (PDS) functions to convert prostaglandin H2 to prostaglandin D2 and has been identified in several studies of CSF (Harrington et al., 1993; Hiraoka et al., 1998); Hiraoka et al., 2001; Kawashima et al., 2001; Mase et al., 1999; Mase et al., 2003; Melegos et al., 1997. Additionally, PDS demonstrates altered isoforms in neurologic disorders including AD and Parkinson's disease.

Because of the increasing importance of AD in our societies, there is a need for new diagnostic tools and efficient AD biomarkers.

SUMMARY OF INVENTION

The purpose of the present invention is to provide novel methods of diagnosing or monitoring AD and related disorders, as well as for predicting and/or assessing the responsiveness of subjects or the efficacy of treatments in subjects having AD or a related disorder.

The inventors have identified a molecular pathway which is involved in the genesis of AD and offers novel targets for development of AD biomarkers.

As indicated herein, an embodiment of the present invention provides a method for the diagnosis of MCI, AD prodrome, AD or methods of aiding in the diagnosis and subclassification of neurological disorders, including AD, by quantifying the amount of a protein, RNA, metabolite, lipid, glucide based biomarker in a biological fluid sample of the subject, such as a cerebrospinal fluid, serum, saliva, urine, etc. and comparing the measured amount with a reference value for the biomarker. The information thus obtained may be used to aid in the diagnosis, or to diagnose the disease, potential drug response or early indications of favourable drug response in the individual. The biomarkers are differentially present in subjects having a neurological disease, including AD, versus subjects free of the disease, or subjects having a different form of dementia.

One embodiment of the present invention is a method of diagnosing or assessing the likelihood that a patient is afflicted with a neurological disease, including AD, the method comprising measuring a level of a protein complex biomarker of the present invention.

Another embodiment of the present invention is a method comprising monitoring the progression of a neurodegenerative disease, including AD, comprising measuring a level of sets of biomarkers of the present invention.

Another embodiment of the present invention comprises monitoring the efficacy of a treatment method of a neurodegenerative disease, including AD, comprising measuring a level of a protein complex biomarker of the present invention.

Another embodiment of the present invention comprises qualifying and sub classifying a neurodegenerative disease, including AD, in a subject, comprising measuring a set of complex biomarker of the present invention.

Typically, biomarkers are selected from disease associated SNPs, proteins, RNAs, metabolites, lipids or glucids involved in synapse biology, angiogenesis or cellular stress response.

In one embodiment, the set of biomarkers of the invention comprises at least two proteins or RNAs encoded by the genes selected from the group consisting of: APBA1, ATG7, BECN1, CD44, CDH2, COL18A1, ERBB4, F3, FLNA, FYN, GRIN2B, IL20, ITPR1, LRP8, MTOR, NPPC, NRP1, PDGFC, ROBO1, SEMA3E, TGFB1, THBS1, VEGFR1 and WWOX.

In another embodiment, the set of biomarkers further comprises at least one further biomarker selected from disease associated SNPs, proteins, RNAs, metabolites, lipids or glucids, detailed below.

In the above and other embodiments of the present invention, the measured level of the biomarker is correlated with neurological disease. In embodiments, this may be accomplished by comparing the measured amount to a reference value for the biomarker. The reference value can be obtained by measuring an amount of the biomarker in age-matched control subjects that are not affected by the disease, or that are free of the disease.

Another embodiment of the present invention comprises monitoring the efficacy of a treatment method of a neurodegenerative disease, including AD, comprising measuring a level of complex set of biomarkers of the present invention. In embodiments, the efficacy of treatment is measured by monitoring levels of the biomarker in the subject compared to a reference, and/or compared to other previous tests of the subject or to an earlier stage of treatment/disease in the subject.

In other aspects, the above method further comprises the step of managing the individual treatment based on the status. For example, if measurement of the set of biomarkers correlates with the presence of sub-type Alzheimer's disease, then managing treatment comprises administering a matched drug or drug combination to slow or revert the progression of the disease. Further measurements can be compared to the previous measurements, or the standard to monitor the progression of the disease.

In a further aspect of the invention, the method further comprises measuring the biomarker after treatment has begun, to monitor the progression of the disease.

In still another aspect, the present invention provides a kit comprising a solid support comprising at least one capture agent attached thereto, wherein the capture agent binds one component of the biomarker protein complex of the present invention.

DETAILED DESCRIPTION OF THE INVENTION

The present invention provides new diagnostic methods and tools for AD and related disorders The term "AD related disorder" designates Alzheimer's disease (AD), senile dementia of AD type (SDAT), Parkinson's disease, Lewis body dementia, vascular dementia, mild cognitive impairment (MCI), prodrome condition of AD, preclinical stage AD, age-associated memory impairment (AAMI) and problem associated with ageing, post-encephalitic Parkinsonism, ALS and Down syndrome.

Rational discovery of potential biomarkers for Alzheimer's disease (AD) is an urgent, unmet demand of modern experimental medicine focused on development of AD-relevant drugs.

Valuable AD biomarkers, allowing detailed monitoring of the disease onset and progression, help to estimate objectively functional effects of tested drugs, to assure a precocious diagnosis of AD and increases efficacy of drug development pipeline, especially the development of drugs designed as a preventive therapy. The main difficulty, decreasing successful rates in disclosing AD-relevant biomarkers, consists in enormous complexity of this neurodegenerative disease, which affects numerous cellular processes in different tissues and provokes profound decline in multitude of physiological parameters.

Very recently, 2010/0124756 US patent application (based on Ray et al., 2007) disclosed the use of a set of 16 proteinacious biomarkers for aiding to AD diagnostic. This set was identified from statistical analysis of signalling protein (cytokines, chemokines and growth factors) levels obtained with commercially available protein chips which are dedicated to study level of circulating cytokines.

The present invention is based on a data mining study that has been done focused on the analysis of pathways which we identified as tightly implicated in AD studying genetic associations and following pangenomic expression profiling experiments. The results are useful for identifying not only proteins, but also metabolites or nucleic acids (RNAs or SNPs) that could be used as biomarkers.

We propose to use a combinatorial data mining approach for selection of potential AD biomarkers and their prioritization for validations studies, based on pathway mining of available experimental data covering results of functional cell biology studies, pan-genomic expression profiling experiments and genetic association studies (Herz & Beffert, 2000; Mattson, 2004; Ballatore et al., 2007; Li et al., 2008). This approach includes a few consecutive steps:

firstly, genes, functionally or genetically associated with AD, are grouped into relevantly small, previously described functional units, which represent minimal signalling transduction modules, these signalling transduction modules are further combined and maximally enlarged, basing on the analysis of publicly available functional studies, to construct AD-relevant pathways, large functional networks of interacting AD-relevant signalling pathways are defined, and individual biomarkers or rational combinations of biomarkers representing different functional networks are prioritized for functional annotation.

Thus, a potential biomarker, —either a protein itself or a product of any biochemical reaction catalyzed by this protein, —is selected and prioritized for validation studies, if it fits the following criteria:

participation in signalling pathway associated with onset and development of AD, participation in the functional network cogently represented by AD-associated pathways, facilitated detection in patient's samples.

Selection of AD-Relevant Biomarkers

Pathway mining analysis revealed that 3 large functional groups of genes, representing several tightly interacting signalling pathways, are associated with development of Alzheimer's disease:

the group of genes implicated in synapse biology that includes genes participating in organization of post-synaptic density zone (PSD), assuring neurotransmitter release and controlling axon growth and guidance, the second group combines genes involved in control of angiogenesis and shares some signalling receptors and their ligands with pathways controlling axon growth and guidance, the third group is constituted by the genes underlying cellular stress response.

Below, we briefly describe exemplar functional networks regulating axon growth and angiogenesis, disclosed by our study.

Functional Network Controlling Axon Growth and Guidance

Proteins participating in regulation of axon growth and guidance allow neuronal precursor cells and axons to migrate toward proper destinations to ensure correct location and connectivity and are involved in developmental maturation of newly established synapses and thus, in execution of cognitive functions.

Consecutive steps of axon growth and guidance are tightly controlled by combined actions of rather limited family of extracellular or membrane-tethered Netrins, Semaphorins, Ephrins, and Slits ligands and their cognate functional receptors. Functional outcomes of activation of majority of axon growth receptors are tightly connected with their ability to differentially modulate activity of small GTPases RhoA, Rac1 and Cdc42, with the RhoA GTPase being mainly responsible for neurite retraction and growth cone collapse in most, though not in all, cellular settings (Leeuwen et al., 1997).

It's necessary to underline that most of these ligands and receptors have an equally important role outside the establishment of neuronal connectivity—namely, in angiogenesis by guiding the growth of newborn blood vessels.

Netrins ligands are secreted proteins that were discovered as regulators of axon extension and cell migration during neural development. They are bifunctional proteins and are capable to act as attractants for some cell types and as repellents for others; the opposite effects of netrins ligands on axon guidance are mediated by two classes of receptors—DCC and UNC5C, both of which were identified by data mining analysis. Axon guidance netrin receptor DCC can be involved in both neurons attraction and repulsion and equally, as it was recently disclosed, participates in regulation of angiogenesis by activating ERK1/2-eNOS signalling module (Nguyen & Cai, 2006). Netrin receptor UNC5C rather possesses neuron repulsion activity (Guan & Rao, 2003).

Then, we identified also two semaphorin ligands SEMA3E and SEMA3C and semaphorin co-receptors neuropilins NRP1 and NRP2 and plexin A2 (PLXNA2), which form functional heteromeric receptor complexes at cellular membrane. Similarly to netrins, class 3 semaphorin ligands are recognized not only as modulators (inhibitors) of axon sprouting, but also as potent modifiers of vascular patterning and, in the case of SEMA3E, selectively interfere with VEGF-induced angiogenesis; other class 3 semaphorins can control vascular morphogenesis rather through inhibition of integrin signalling (Moriya et al., 2007; Acevedo et al., 2008).

Further, we revealed also several members of ephrin signalling pathways, —for instance, ephrin receptor EPHA3 and accessory proteins implicated in ephrin signalling NGEF and RhoGEF kinase KALIRIN, —which mediate growth cones collapse and repulsion in nervous system during development and play an important role in synaptic plasticity in adult CNS (Winning et al., 2002; Noren & Pasquale, 2004).

As well, we identified a compact functional module representing Slit/Robo signalling pathway, involved simultaneously in axons repulsion and branching—roundabout ROBO2 axon guidance receptor, its ligand SLIT1 and their down-stream target Slit/Robo Rho GTPase activating protein 3 (Brose & Tessier-Lavigne, 2000).

Regulation of axon growth and guidance by netrins, slits, semaphorins and ephrins proteins is executed through complex, combinatorial interactions of their cognate receptors that integrate information from different families of guidance cues. For instance, Slit ligands induce direct binding of Robo receptors to DCC, and thus silence DCC guidance response to netrins (Stein & Tessier-Lavigne, 2001). Combinatorial assembly of semaphorin receptors was shown to modify their specificity and affinity to available ligands. Moreover, combinatorial action of axon guidance receptors in signalling complexes can even change the polarity of a guidance response from attraction to repulsion, as it was demonstrated in the case of netrin's signalling, where dimerization of the DCC receptor with UNC5C receptor converts DCC-mediated netrin-induced growth cone attraction to repulsion (Hong et al., 1999).

These examples clearly demonstrate that signalling pathways revealed by our data mining approach are not just mechanistically united into the same functional group, but really form an integrated functional network, where signalling modules co-operatively direct axon growth and guidance process.

Functional Network Controlling Angiogenesis

Angiogenesis plays a fundamental role in ensuring tissue homeostasis and in adaptive responses to environmental and physiological challenges such as hypoxia or wound healing; its dysfunction contributes to the pathogenesis of numerous and heterogeneous pathologies varying from cardiovascular complications to tumour's growth and metastasis.

Although Alzheimer's disease is traditionally considered as a neurodegenerative condition accompanied by collateral vascular pathology, our data allow re-evaluating the pathogenic impact of the vascular deregulation and attribute an important, probably, causative role to angiogenic pathways in aetiology of Alzheimer's disease, comparable with the role played by dysfunction of neuronal signalling. We found that genes regulating angiogenesis are extremely enriched in signalling networks implicated in Alzheimer's disease: this conclusion calls not only for revising traditional approaches for prevention and curing of Alzheimer disease, but as well provides new guidelines for selection of pertinent biomarkers for detailed monitoring of onset and progression of this complex neurodegenerative disorder.

For instance, we identified CD44 gene that encodes a receptor for hyaluronic acid (HA), whose degradation products promote angiogenesis (West et al., 1985). This receptor was implicated in the organization and/or stabilization of the endothelia of forming or newly formed vessels (Cao et al., 2006). CD44 receptor can also bind and regulates activity of proteins such as osteopontin, collagens, and matrix metalloproteinases (MMPs) implicated in extracellular matrix dynamic, which ultimately accompanies formation of new blood vessels (Sottile, 2004).

Other membrane receptors, implicated in control of angiogeneis and identified by data mining approach, include IL20Rα, leptin LEPTR receptor, endothelin EDNRA receptor and VEGFR1/FLT1 receptor, as well as a functional ligand for Tie-2 receptor (ANGPT2 protein) affecting vascular remodelling (Fiedler et al., 2003). IL20Rα gene encodes a receptor for IL20, a pleiotropic cytokine involved in vascular tube formation (Hsieh et al., 2006). Leptin, an endocrine hormone and ligand for LEPTR, stimulates angiogenesis synergistically with fibroblast growth factor FGF-2 and vascular endothelial growth factor (VEGF), the two most potent and ubiquitously expressed angiogenic factors. As well, it is involved in the increase of vascular permeability (Cao et al., 2001). Endothelin-1, a ligand for EDNRA receptor, plays a major role in tumor proliferation and angiogenesis of various types of cancer. NRP1 and NRP2 are transmembrane co-receptors not only for semaphorins, but also for VEGF growth factors and modulate VEGFR-2 signalling activation, which assures developmental angiogenesis (Ferrara et al., 2003). Angiopoietin-1 (ANGPTA) and angiopoietin-2 (ANGPT2) have been identified as master regulators with different effector functions on the vascular assembly. All these signalling pathways are known to be tightly integrated in global functional network regulating different aspects of endothelial cells biology.

Additionally, we also selected a group of genes (THBS2, LAMA1, COL4A2, ADAMTS12 and ADAM10) involved in organization and remodelling of extracellular matrix, an obligatory step in remodelling of vascular patterning, or in functional processing (TLL2) of well-known angiogenic modulators such as prolactin, growth hormone, and placental lactogen (Sottile, 2004; Ge et al., 2007).

Finally, we identified also a large number of genes, involved in LPA/S1P metabolism or modulated by LPA/S1P signaling (MTR, MAT2B, CUBN, ATP10A, THEM2, PITPNC1, ENPPG, SGPP2, AGPAT, DGKH, DGKB, MGST2, PLD2, and DRD2). Phosphatidic acid (PA), lysophosphatidic acid (LPA), and sphingosine 1-phosphate (S1P) are natural phospholipids that possess potent signaling properties. Notably, these phospholipid growth factors display divergent effects on angiogenic potential of endothelial cells and could—in complementary, combined manner—effectively induce neovascularization. For instance, S1P is mainly involved in promotion of chemotactic migration of endothelial cells, while LPA is more implicated in stabilization of endothelial monolayer barrier function at late stages in angiogenesis (English et al., 1999). LPA could affect angiogenesis either by modulating activity of RhoA GTPase or by enhancing expression of several angiogenic factors—VEGF, PDGFB and IL-8 (Park et al., 2007). Besides its tight involvement in angiogenesis, LPA is also recognized as an extracellular lipid signaling provoking neurite growth cone collapse and influencing migration of early postmitotic neurons during development (Fukushima et al., 2002).

Again, as in the case of axon growth/guidance signalling, these individual pro- or anti-angiogenic factors, revealed by pathway data mining, are integrated into a unique network of functional pathways co-operatively governing development of vascular system.

Classes of AD-Relevant Biomarkers

Given examples clearly demonstrate that disclosing of the functional networks, associated with development of Alzheimer's disease, provide clear guidelines for rational selection and prioritization of individual biomarkers or their combinations for experimental validation studies. For instance, as evidenced by our data, axon growth receptors or receptors controlling different stages of angiogenesis, or their ligands, or shedding extracellular domains of these receptors generated by metalloproteinases or through regulated intra-membranous proteolysis, or metabolites from LPA/S1P biochemical pathways represent pertinent functional biomarkers allowing precise and objective monitoring of consecutive stages of onset and development of AD.

We present 3 lists of preferred AD-relevant biomarkers. The 1st class of biomarkers comprises genes, organized in cellular pathways that are associated with onset or progression of Alzheimer's disease. The functional partners of these genes were revealed by the manual mining of available experimental data and by pangenomic expression profiling or protein interaction studies and constitute the $2^{nd}$ class of biomarkers. Finally, the 3rd class of AD-relevant markers contains potential partners of genes from the 1st class, disclosed by pangenomic expression profiling or protein interaction studies and selected additionally for their ability to be detected in blood cells and other biofluids.

TABLE 1

Class 1 - Gene associated with onset or progression of AD:

ABAT (EG: 18), ABCA1 (EG: 19), ABCC4 (EG: 10257), ABCC9 (EG: 10060),
ACADSB (EG: 36), ACC2/ACACB (EG: 32), ACCN1 (EG: 40), ACCN2 (EG: 41),
ACOT11 (EG: 26027), ACOT7 (EG: 11332), ACOXL (EG: 55289), ACYP2 (EG: 98),
ADAM12 (EG: 8038), ADAMTS12 (EG: 81792), ADARB2 (EG: 105), ADCY2
(EG: 108), ADH5 (EG: 128), ADRA1A (EG: 148), AGPAT5 (EG: 55326), AGPAT7
(EG: 254531), AKAP11 (EG: 11215), AKAP13 (EG: 11214), AKAP2 (EG: 11217),
ALCAM (EG: 214), ALK (EG: 238), ALX4 (EG: 60529), ANG2/ANGPT2 (EG: 285),
ANK1 (EG: 286), ANKS1A (EG: 23294), ANXA1 (EG: 301), ANXA3 (EG: 306),
APBA1 (EG: 320), APBA2BP/NECAB3 (EG: 63941), APBA3 (EG: 9546), APBB1
(EG: 322), APPBP2 (EG: 10513), ARHGAP10 (EG: 79658), ARHGAP17 (EG: 55114),
ARHGAP18 (EG: 93663), ARHGAP22 (EG: 58504), ARHGAP26 (EG: 23092), ARNT2
(EG: 9915), ASAH1 (EG: 427), ATF3 (EG: 467), ATF7 (EG: 11016), ATG10
(EG: 83734), ATG5 (EG: 9474), ATG7 (EG: 10533), ATIC (EG: 471), ATP10A
(EG: 57194), ATP10B (EG: 23120), ATP10D (EG: 57205), ATP2A3 (EG: 489), ATP2B1
(EG: 490), ATP2B2-EG: 491), ATP6V1C1 (EG: 528), ATP7B (EG: 540), ATR
(EG: 545), ATXN1 (EG: 6310), AUH (EG: 549), B3GNTL1 (EG: 146712), BAI3
(EG: 577), BAP1 (EG: 8314), BCL2 (EG: 596), BCL2L14 (EG: 79370), BCL3 (EG: 602),
BDH2 (EG: 56898), BDNF (EG: 627), BIN1 (EG: 274), BMP3A (EG: 651), BRE
(EG: 9577), BRI3BP (EG: 140707), BRIP1 (EG: 83990), CA10 (EG: 56934), CACNA1C
(EG: 775), CACNA1D (EG: 776), CACNA1E (EG: 777), CACNA2D1 (EG: 781),
CACNA2D3 (EG: 55799), CACNA2D4 (EG: 93589), CACNB2 (EG: 783), CADPS2
(EG: 93664), CALCB (EG: 797), CALCR (EG: 799), CALN1 (EG: 83698), CAMK1D
(EG: 57118), CAMK2D (EG: 817), CAMK4 (EG: 814), CAMKK2 (EG: 10645), CAST1
(EG: 26059), CD44 (EG: 960), CDC42EP3 (EG: 10602), CDH10 (EG: 1008), CDH12
(EG: 1010), CDH13 (EG: 1012), CDH18 (EG: 1016), CDH22 (EG: 64405), CDH4
(EG: 1002), CDH5 (EG: 1003), CDH8 (EG: 1006), CDH9 (EG: 1007), CDK5RAP2
(EG: 55755), CDK6 (EG: 1021), CDKAL1 (EG: 54901), CDON (EG: 50937), CHL1
(EG: 10752), CHMP5 (EG: 51510), CHRM2 (EG: 1129), CITRON (EG: 11113), CLTC
(EG: 1213), CNGB3 (EG: 54714), CNTFR (EG: 1271), CNTN4 (EG: 152330), COL3A1
(EG: 1281), COL4A2 (EG: 1284), COL4A3BP (EG: 10087), COLEC12 (EG: 81035),
COMMD1 (EG: 150684), COMMD10 (EG: 51397), COPS7A (EG: 50813), COPS7B
(EG: 64708), CS (EG: 1431), CSH1 (EG: 1442), CSMD1 (EG: 64478), CST5 (EG: 1473),
CTNNA2 (EG: 1496), CTNND2 (EG: 1501), CUBN (EG: 8029), CUGBP2 (EG: 10659),
CYP11A1 (EG: 1583), CYP19A1 (EG: 1588), CYP1B1 (EG: 1545), CYP7B1 (EG: 9420),
DAAM1 (EG: 23002), DAB1 (EG: 1600), DAPK1 (EG: 1612), DAPK2 (EG: 23604),
DBC1 (EG: 1620), DBT (EG: 1629), DCC (EG: 1630), DEPDC2 (EG: 80243), DGKB
(EG: 1607), DGKE (EG: 8526), DGKG (EG: 1608), DGKH (EG: 160851), DHCR7
(EG: 1717), DISC1 (EG: 27185), DLD (EG: 1738), DLG2 (EG: 1740), DLGAP1
(EG: 9229), DNAJB11 (EG: 51726), DNER (EG: 92737), DNM3 (EG: 26052), DOCK2
(EG: 1794), DOCK4 (EG: 9732), DOCK9 (EG: 23348), DPP6 (EG: 1804), DRD2
(EG: 1813), EDNRA (EG: 1909), EFNA5 (EG: 1946), EGFR (EG: 1956), EHHADH

TABLE 1-continued

Class 1 - Gene associated with onset or progression of AD:

(EG: 1962), ELAVL2 (EG: 1993), EML1 (EG: 2009), ENAH (EG: 55740), ENPP2/
autotaxin (EG: 5168), ENPP6 (EG: 133121), ENPP7 (EG: 339221), EPB41L2 (EG: 2037),
EPHA10 (EG: 284656), EPHA3 (EG: 2042), EPHA6 (EG: 285220), ERBB4 (EG: 2066),
ETFA (EG: 2108), EYA2 (EG: 2139), F13A1 (EG: 2162), FABP5 (EG: 2171), FBLN2
(EG: 2199), FBXW8 (EG: 26259), FER1L3 (EG: 26509), FGF12 (EG: 2257), FGF14
(EG: 2259), FGF5 (EG: 2250), FHIT (EG: 2272), FLNB (EG: 2317), FMN1 (EG: 342184),
FOXO3A (EG: 2309), FREQ (EG: 23413), FRS2 (EG: 10818), FSTL5 (EG: 56884), FTO
(EG: 79068), FZD3 (EG: 7976), GAB2 (EG: 9846), GABBR2 (EG: 9568), GABRA2
(EG: 2555), GABRB2 (EG: 2561), GABRB3 (EG: 2562), GABRG3 (EG: 2567), GATA3
(EG: 2625), GDF10 (EG: 2662), GDF2 (EG: 2658), GIPC2 (EG: 54810), GLI2
(EG: 2736), GLRA1 (EG: 2741), GLRX (EG: 2745), GLUD1 (EG: 2746), GNG12
(EG: 55970), GNPTAB (EG: 79158), GPC5 (EG: 2262), GPC6 (EG: 10082), GRIA4
(EG: 2893), GRID1 (EG: 2894), GRID2 (EG: 2895), GRIK1 (EG: 2897), GRIK2
(EG: 2898), GRIK3 (EG: 2899), GRIK4 (EG: 2900), GRIN2B (EG: 2904), GRM7
(EG: 2917), GRM8 (EG: 2918), GUCY1B2 (EG: 2974), GULP1 (EG: 51454), HAPLN1
(EG: 1404), HAS2 (EG: 3037), HBG2 (EG: 3048), HCRTR2 (EG: 3062), HECW1
(EG: 23072), HEY2 (EG: 23493), HIF1A (EG: 3091), HIPK1 (EG: 204851), HIPK2
(EG: 28996), HIVEP2 (EG: 3097), HK2 (EG: 3099), HMBOX1 (EG: 79618), HMOX1
(EG: 3162), HPSE2 (EG: 60495), HRG (EG: 3273), HSD17B12 (EG: 51144), HTR1A
(EG: 3350), IDE (EG: 3416), IGF1R (EG: 3480), IGF2BP1(EG: 10642), IL18R1
(EG: 8809), IL20RA (EG: 53832), IL20RB (EG: 53833), INPP4A (EG: 3631), INPP4B
(EG: 8821), INSR (EG: 3643), IPPK (EG: 64768), IQGAP2 (EG: 10788), ITGA1
(EG: 3672), ITGA11 (EG: 22801), ITGA9 (EG: 3680), ITPR1 (EG: 3708), ITPR2
(EG: 3709), JAK1 (EG: 3716), JARID1B (EG: 10765), KALIRIN/KALRN (EG: 8997),
KCND2 (EG: 3751), KCNJ6 (EG: 3763), KCNMA1 (EG: 3778), KREMEN1
(EG: 83999), KTN1 (EG: 3895), KYNU (EG: 8942), LAMA1 (EG: 284217), LAMA3
(EG: 3909), LEPR (EG: 3953), LETMD1 (EG: 25875), LIPL3/LIPM (EG: 340654),
LPHN2 (EG: 23266), LRP1 (EG: 4035), LTBP1 (EG: 4052), LTBP2 (EG: 4053),
MAD1L1 (EG: 8379), MAML3 (EG: 55534), MAP2 (EG: 4133), MAT2B (EG: 27430),
MBNL2 (EG: 10150), MCC1 (EG: 4163), MCPH1 (EG: 79648), MDM1 (EG: 56890),
ME1 (EG: 4199), ME2 (EG: 4200), MGLL (EG: 11343), MGST2 (EG: 4258), MMP10
(EG: 4319), MMP7 (EG: 4316), MSR1 (EG: 4481), MTOR (EG: 2475), MTR (EG: 4548),
MTRR (EG: 4552), MYO10 (EG: 4651), NAALAD2 (EG: 10003), NAV1 (EG: 89796),
NBEA (EG: 26960), NCK1 (EG: 4690), NCK2 (EG: 8440), NCOA1 (EG: 8648), NEDD4
(EG: 4734), NEDD9 (EG: 4739), NFATC2 (EG: 4773), NFKB1 (EG: 4790), NFYB
(EG: 4801), NGEF (EG: 25791), NISCH (EG: 11188), NLGN1 (EG: 22871), NOG
(EG: 9241), NOS1AP (EG: 9722), NOX3 (EG: 50508), NPPC (EG: 4880), NR3C2
(EG: 4306), NRCAM (EG: 4897), NRG1 (EG: 3084), NRG3 (EG: 10718), NRG4
(EG: 145957), NRIP1 (EG: 8204), NRP1 (EG: 8829), NRP2 (EG: 8828), NRXN1
(EG: 9378), NRXN3 (EG: 9369), NUDT1 (EG: 4521), NUDT13 (EG: 25961), NUDT3
(EG: 11165), ODZ2 (EG: 57451), OGDH (EG: 4967), OPCML (EG: 4978), OPRM1
(EG: 4988), OSBPL10 (EG: 114884), OSBPL3 (EG: 26031), OSTN (EG: 344901),
P2RX4 (EG: 5025), P2RY12 (EG: 64805), PAFAH2 (EG: 5051), PAK6 (EG: 56924),
PAK7 (EG: 57144), PALLD (EG: 23022), PARK2 (EG: 5071), PARVA (EG: 55742), PC
(EG: 5091), PCDH9 (EG: 5101), PCLO (EG: 27445), PCSK5 (EG: 5125), PDE11A
(EG: 50940), PDE1A (EG: 5136), PDE3A (EG: 5139), PDE4D (EG: 5144), PDE6D
(EG: 5147), PDGFC (EG: 56034), PFKP (EG: 5214), PICALM (EG: 8301), PIK3C2G
(EG: 5288), PIK3C3 (EG: 5289), PIP5K2A (EG: 5305), PISD (EG: 23761), PITPNC1
(EG: 26207), PLA2R1 (EG: 22925), PLCB1 (EG: 23236), PLCL1 (EG: 5334), PLD2
(EG: 5338), PLEKHA6 (EG: 22874), PLXDC2 (EG: 84898), PLXNA2 (EG: 5362), PML
(EG: 5371), PPFIA2 (EG: 8499), PPFIBP1 (EG: 8496), PPFIBP2 (EG: 8495), PPM1D
(EG: 8493), PPM1E (EG: 22843), PPP1R12A (EG: 4659), PRIMA1 (EG: 145270),
PRKD3 (EG: 23683), PRKG1 (EG: 5592), PRLR (EG: 5618), PRNP (EG: 5621), PSAP
(EG: 5660), PSD3 (EG: 23362), PTK2 (EG: 5747), PTN (EG: 5764), PTPRG (EG: 5793),
PTPRM (EG: 5797), PVRL1 (EG: 5818), RAB3B (EG: 5865), RALA (EG: 5898),
RALBP1 (EG: 10928), RASGRF2 (EG: 5924), RBBP8 (EG: 5932), RGS8 (EG: 85397),
RIMS1 (EG: 22999), RIMS2 (EG: 9699), ROBO1 (EG: 6091), ROBO2 (EG: 6092),
ROR1 (EG: 4919), ROR2 (EG: 4920), RPH3AL (EG: 9501), RPS6KA2 (EG: 6196),
RPS6KA5 (EG: 9252), RPS6KB1 (EG: 6198), RPSA (EG: 3921), RTN1 (EG: 6252),
RUNX2 (EG: 860), RYR2 (EG: 6262), SCAP2 (EG: 8935), SCARF2 (EG: 91179),
SCGB1A1 (EG: 7356), SCHIP1 (EG: 29970), SCN11A (EG: 11280), SCN9A (EG: 6335),
SDHA (EG: 6389), SDK1 (EG: 221935), SEC24D (EG: 9871), SEMA3A (EG: 10371),
SEMA3C (EG: 10512), SEMA3E (EG: 9723), SEMA5A (EG: 9037), SEMA7A
(EG: 8482), SERPINA6 (EG: 866), SERPINC1 (EG: 462), SFRP4 (EG: 6424), SGMS1
(EG: 259230), SGPP2 (EG: 130367), SH3BP5 (EG: 9467), SHMT1 (EG: 6470), SIL1
(EG: 64374), SLC6A6 (EG: 9990), SLC1A1 (EG: 6505), SLC1A2 (EG: 6506), SLC1A3
(EG: 6507), SLC1A4 (EG: 6509), SLC22A4 (EG: 6583), SLC24A3 (EG: 57419),
SLC25A21 (EG: 89874), SLC6A1 (EG: 6529), SLC6A18 (EG: 348932), SLC6A20
(EG: 54716), SLC6A7 (EG: 6534), SLC8A1 (EG: 6546), SLIT 1 (EG: 6585), SMAD4
(EG: 4089), SMYD3 (EG: 64754), SNCA (EG: 6622), SNCAIP (EG: 9627), SND1
(EG: 27044), SNPH (EG: 9751), SNX9 (EG: 51429), SOCS1 (EG: 8651), SORBS1
(EG: 10580), SORBS2 (EG: 8470), SORCS1 (EG: 114815), SORCS2 (EG: 57537), SOX5
(EG: 6660), SOX9 (EG: 6662), SPOCK1 (EG: 6695), SPOCK3 (EG: 50859), SQSTM1
(EG: 8878), SRD5A1 (EG: 6715), SRGAP3 (EG: 9901), ST14 (EG: 6768), STAB2
(EG: 55576), STAT3 (EG: 6774), STX2 (EG: 2054), STXBP6 (EG: 29091), SV2B
(EG: 9899), SV2C (EG: 22987), SYN3 (EG: 8224), SYT12 (EG: 91683), SYT2
(EG: 127833), TBXAS1 (EG: 6916), TFCP2 (EG: 7024), TGFBRAP1 (EG: 9392),
THBS2 (EG: 7058), THEM2 (EG: 55856), TLL2 (EG: 7093), TNFAIP3 (EG: 7128),

TABLE 1-continued

Class 1 - Gene associated with onset or progression of AD:

TNFRSF11B (EG: 4982), TRIO (EG: 7204), TRKB/NTRK2 (EG: 4915), TRPM3 (EG: 80036), TRPS1 (EG: 7227), UBE3A (EG: 7337), ULK4 (EG: 54986), UNC13C (EG: 440279), UNC5C (EG: 8633), VAMP5 (EG: 10791), VANGL2 (EG: 57216), VAV3 (EG: 10451), VDAC2 (EG: 7417), VEGFR1/FLT1 (EG: 2321), VEGFR2 (EG: 3791), VIL2 (EG: 7430), VPS13B (EG: 157680), WASPIP/WIPF1 (EG: 7456), WIF1 (EG: 11197), WWOX (EG: 51741), YES1 (EG: 7525), ZFHX1B (EG: 9839).

TABLE 2

Class 2 - Functional partner genes:

ABL1 (EG: 25), A2M (EG: 2), ABI1 (EG: 10006), ACAT1 (EG: 38), ACHE (EG: 43), ACTN1 (EG: 87), ACTN2 (EG: 88), ACTN3 (EG: 89), ACTN4 (EG: 81), ADAM10 (EG: 102), ADAM17 (EG: 6868), ADAM9 (EG: 8754), ADIPOQ (EG: 9370), ADIPOR1 (EG: 51094), ADIPOR2 (EG: 79602), ADORA2B (EG: 136), ADRB2 (EG: 154), ADRBK1 (EG: 156), AKR1C2 (EG: 1646), AKT1 (EG: 207), ALDH2 (EG: 217), ALOX12 (EG: 239), ANKRA2 (EG: 57763), APH1A (EG: 51107), APH1B (EG: 83464), APOA1 (EG: 335), APOE (EG: 348), APP (EG: 351), ARHGEF11 (EG: 9826), ARHGEF12 (EG: 23365), ATG12 (EG: 9140), ATM (EG: 472), ATP1A1 (EG: 476), BACE1 (EG: 23621), BACE2 (EG: 25825), BAD (EG: 572), BAK (EG: 578), BAX (EG: 581), BCAR1 (EG: 9564), BECN1 (EG: 8678), BGLAP (EG: 632), BMP2 (EG: 650), BRCA1 (EG: 672), BSN (EG: 8927), CALM1 (EG: 801), CASK (EG: 8573), CASP3 (EG: 836), CASP8 (EG: 841), CASR (EG: 846), CBL (EG: 867), CCNE1 (EG: 898), CD36 (EG: 948), CDC2 (EG: 983), CDC42 (EG: 998), CDC42BPB (EG: 9578), CDH1 (EG: 999), CDH2 (EG: 1000), CDK5 (EG: 1020), CDKN1A (EG: 1026), CHAT (EG: 1103), CHEK1 (EG: 1111), CHRM1 (EG: 1128), CHRM3 (EG: 1131), CHRM4 (EG: 1132), CHRM5 (EG: 1133), CLTA (EG: 1211), CLTB (EG: 1212), COL18A1 (EG: 80781), CPT1A (EG: 1374), CPT1B (EG: 1375), CREB1 (EG: 1385), CRMP1 (EG: 1400), CSF1 (EG: 1435), CSNK1A1 (EG: 1452), CTNN (EG: 2017), CTNNB1 (EG: 1499), CTTN (EG: 2017), CUL1 (EG: 8454), CYSLTR1 (EG: 10800), CYSLTR2 (EG: 57105), DGKZ (EG: 8525), DHFR (EG: 1719), DLG3 (EG: 1741), DLG4 (EG: 1742), DLGAP2 (EG: 9228), DLGAP3 (EG: 58512), DLGAP4 (EG: 22839), DNAJB9 (EG: 4189), DNM1 (EG: 1759), DOCK3 (EG: 1795), DRD5 (EG: 1816), DVL1 (EG: 1855), EDG1 (EG: 1901), EDG2 (EG: 1902), EDG3 (EG: 1903), EDG4 (EG: 9170), EDG5 (EG: 9294), EDG6 (EG: 8698), EDG7 (EG: 23566), EDG8 (EG: 53637), EDN1 (EG: 1906), EDNRB (EG: 1910), EFNA1 (EG: 1942), EFNA2 (EG: 1943), EFNA3 (EG: 1944), EFNA4 (EG: 1945), EFNB1 (EG: 1947), EFNB2 (EG: 1948), EFNB3 (EG: 1949), EGF (EG: 1950), EIF4E (EG: 1977), EIF4EBP1 (EG: 1978), EPHA1 (EG: 2041), EPHA2 (EG: 1969), EPHA4 (EG: 2043), EPHA5 (EG: 2044), EPHA7 (EG: 2045), EPHA8 (EG: 2046), EPHB1 (EG: 2047), EPHB2 (EG: 2048), EPHB3 (EG: 2049), EPHB4 (EG: 2050), EPHB6 (EG: 2051), ERC1 (EG: 23085), ERC2 (EG: 26059), ESRRG (EG: 2104), EZR (EG: 7430), F2 (EG: 2147), F2R (EG: 2149), F3 (EG: 2152), FAS (EG: 355), FDPS (EG: 2224), FES (EG: 2242), FGF2 (EG: 2247), FGF4 (EG: 2249), FGFR1 (EG: 2260), FKBP1A (EG: 2280), FKBP1B (EG: 2281), FLNA (EG: 2316), FOXO1 (EG: 2308), FRAP1 (EG: 2475), fusion of IL16 (EG: 3603) with PDZ domain, FYN (EG: 2534), FZD2 (EG: 2535), GADD45A (EG: 1647), GADD45B (EG: 4616), GADD45G (EG: 10912), GDNF (EG: 2668), GFRA1 (EG: 2674), GFRA2 (EG: 2675), GFRA3 (EG: 2676), GFRA4 (EG: 64096), GH1 (EG: 2688), GNA12 (EG: 2768), GNA13 (EG: 10672), GNAI1 (EG: 2770), GNAI2 (EG: 2771), GNAI3 (EG: 2773), GNB2L1 (EG: 10399), GOPC (EG: 57120), GPR37 (EG: 2861), GRIA2 (EG: 2891), GRIA3 (EG: 2892), GRIN3A (EG: 116443), GRIP1 (EG: 23426), GRIP2 (EG: 80852), GRK4 (EG: 2868), GRK5 (EG: 2869), GRM3 (EG: 2913), GRM5 (EG: 2915), GRM6 (EG: 2916), GSK3B (EG: 2932), GUCY2C (EG: 2984), GUCY2D (EG: 3000), GUCY2E (EG: 390226), GUCY2F (EG: 2986), GUCY2G (EG: 390003), HGF (EG: 3082), HOMER1 (EG: 9456), HOXD13 (EG: 3239), HSD11B1 (EG: 3290), HSP90B1 (EG: 7184), HSPA4L (EG: 22824), HSPA5 (EG: 3309), HTR1B (EG: 3351), HTR1D (EG: 3352), HYAL1 (EG: 3373), HYAL2 (EG: 8692), HYAL3 (EG: 8372), HYAL4 (EG: 23553), HYOU1 (EG: 10525), IGF2 (EG: 3481), IL16 (EG: 3603), IL20 (EG: 50604), IL6ST (EG: 3572), IL8 (EG: 3576), IMPDH1 (EG: 3614), IMPDH2 (EG: 3615), INS (EG: 3630), IQGAP1 (EG: 8826), IQUB (EG: 154865), IRF1 (EG: 3659), ITCH (EG: 83737), ITGA6 (EG: 3655), ITGB1 (EG: 3688), KCNA2 (EG: 3737), KCNIP1 (EG: 30820), KCNIP2 (EG: 30819), KCNJ11 (EG: 3767), KCNJ12 (EG: 3768), KCNJ8 (EG: 3764), KCNMB1 (EG: 3779), LDLR (EG: 3949), LEP (EG: 3952), LIFR (EG: 3977), LIN7A (EG: 8825), LIN7B (EG: 64130), LIN7C (EG: 55327), LPIN1 (EG: 23175), LPIN2 (EG: 9663), LPIN3 (EG: 64900), LRP2 (EG: 4036), LRP6 (EG: 4040), LRP8 (EG: 7804), LYN (EG: 4067), MAOA (EG: 4128), MAOB (EG: 4129), MAPK1 (EG: 5594), MAPK12 (EG: 6300), MAPK3 (EG: 5595), MAPK8 (EG: 5599), MAPT (EG: 4137), MET (EG: 4233), MLH1 (EG: 4292), MLLT4 (EG: 4301), MME (EG: 4311), MMP2 (EG: 4313), MMP3 (EG: 4314), MMP9 (EG: 4318), MSN (EG: 4478), MUC1 (EG: 4582), MYCBP2 (EG: 23077), MYL1 (EG: 4632), NCAM1 (EG: 4684), NCF2 (EG: 4688), NCSTN (EG: 23385), NF2 (EG: 4771), NGF (EG: 4803), NGFR (EG: 4804), NOS1 (EG: 4842), NOS3 (EG: 4846), NOTCH1 (EG: 4851), NOTCH2 (EG: 4853), NOTCH3 (EG: 4854), NOVA1 (EG: 4857), NOX1 (EG: 27035), NOX4 (EG: 50507), NPPA (EG: 4878), NPPB (EG: 4879), NR1I2 (EG: 8856), NR3C1 (EG: 2908), NRAS (EG: 4893), NTF3 (EG: 4908), NTN1 (EG: 9423), NTN2L (EG: 4917),

TABLE 2-continued

Class 2 - Functional partner genes:

NTN3 (EG: 4917), OPRK1 (EG: 4986), OPRS1 (EG: 10280), P2RY1 (EG: 5028), PAK1 (EG: 5058), PCAF (EG: 8850), PCTP (EG: 58488), PDE5A (EG: 8654), PDGFA (EG: 5154), PDGFB (EG: 5155), PDGFRA (EG: 5156), PDGFRB (EG: 5159), PIAS1 (EG: 8554), PICK1 (EG: 9463), PIK3CA (EG: 5290), PIK3CB (EG: 5291), PIK3R1 (EG: 5295), PIK3R4 (EG: 30849), PIP5K1A (EG: 8394), PIP5K1B (EG: 8395), PLA2G1B (EG: 5319), PLA2G2A (EG: 5320), PLA2G4A (EG: 5321), PLA2G5 (EG: 5322), PLA2G6 (EG: 8398), PLAT (EG: 5327), PLAU (EG: 5328), PLD1 (EG: 5337), PLG (EG: 5340), PLN (EG: 5350), PPAP2A (EG: 8611), PPAP2B (EG: 8613), PPAP2C (EG: 8612), PPARA (EG: 5465), PPARG (EG: 5468), PPARGC1B (EG: 133522), PPP1CA (EG: 5499), PPP3CA (EG: 5530), PPP3CB (EG: 5532), PPP3CC (EG: 5533), PRKAA1 (EG: 5562), PRKAA2 (EG: 5563), PRKAB1 (EG: 5564), PRKAB2 (EG: 5565), PRKACA (EG: 5566), PRKACB (EG: 5567), PRKAG1 (EG: 5571), PRKCA (EG: 5578), PRKCD (EG: 5580), PRL (EG: 5617), PSEN1 (EG: 5663), PSEN2 (EG: 5664), PSENEN (EG: 55851), PTGS2 (EG: 5743), PTK2B (EG: 2185), PTPN11 (EG: 5781), PTPRF (EG: 5792), PXN (EG: 5829), RAC1 (EG: 5879), RAP1A (EG: 5906), RAP1B (EG: 5908), RBPJ (EG: 3516), RDX (EG: 5962), RELN (EG: 5649), RET(EG: 5979), RGNEF (EG: 64283), RHEB (EG: 6009), RHOA (EG: 387), RHOG (EG: 391), ROCK1 (EG: 6093), ROCK2 (EG: 9475), RPH3A (EG: 22895), RPS6KA1 (EG: 6195), RPS6KB2 (EG: 6199), RPTOR (EG: 57521), RYR3 (EG: 6263), SCARB1 (EG: 949), SCN1A (EG: 6323), SCN1B (EG: 6324), SEMA3F (EG: 6405), SEMA4A (EG: 64218), SEMA4B (EG: 10509), SEMA4C (EG: 54910), SEMA5B (EG: 54437), SEMA6B (EG: 10501), SEMA6C (EG: 10500), SERPINA5 (EG: 5104), SERPINB2 (EG: 5055), SERPIND1 (EG: 3053), SERPINE1 (EG: 5054), SERPINE2 (EG: 5270), SH3GL2 (EG: 6456), SHH (EG: 6469), SIAH1 (EG: 6477), SLC8A2 (EG: 6543), SLC9A1 (EG: 6548), SLC9A3R1 (EG: 9368), SLC9A3R2 (EG: 9351), SLN (EG: 6588), SMAD3 (EG: 4088), SMAD5 (EG: 4090), SNAP25 (EG: 6616), SOX6 (EG: 55553), SPP1 (EG: 6696), SRC (EG: 6714), SREBF1 (EG: 6720), SREBF2 (EG: 6721), STAR (EG: 6770), STAT5A (EG: 6776), STAT5B (EG: 6777), STK11 (EG: 6794), STX1A (EG: 6804), STXBP1 (EG: 6812), SUMO1 (EG: 7341), SYNJ1 (EG: 8867), SYNJ2 (EG: 8871), SYTL4 (EG: 94121), TBR1 (EG: 10716), TGFB1 (EG: 7040), TGFBR1 (EG: 7046), TGFBR2 (EG: 7048), TGFBR3 (EG: 7049), THBS1 (EG: 7057), THRA (EG: 7067), THRB (EG: 7068), TIAM1 (EG: 7074), TIMP2 (EG: 7077), TNF (EG: 7124), TNFRSF11A (EG: 8792), TNFRSF21 (EG: 27242), TNFSF11 (EG: 8600), TP53 (EG: 7157), TP63 (EG: 8626), TRAF6 (EG: 7189), TRPC3 (EG: 7222), TRPC4 (EG: 7223), TRPC5 (EG: 7224), TSC1 (EG: 7248), TSC2 (EG: 7249), TSPO (EG: 706), UBE2A (EG: 7319), UNC13B (EG: 10497), VAMP2 (EG: 6844), VCL (EG: 7414), VDR (EG: 7421), VEGFA (EG: 7422), VEGFB (EG: 7423), VEGFC (EG: 7424), VEZF1 (EG: 7716), WASF1 (EG: 8936), WNT1 (EG: 7471), WNT5A (EG: 7474), XDH (EG: 7498), YAP1 (EG: 10413).

TABLE 3

Class 3 - Potential partners of Class 1 genes:

A4GALT (EG: 53947), ABCB1 (EG: 5243), ACACA (EG: 31), ACADM (EG: 34), ACAT2 (EG: 39), ACTB (EG: 60), ACTG1 (EG: 71), ADAM15 (EG: 8751), ADCY1 (EG: 107), ADCY5 (EG: 111), ADORA1 (EG: 134), ADORA2A (EG: 135), AGA (EG: 175), AHCY (EG: 191), AHSG (EG: 197), AK2 (EG: 204), AKAP3 (EG: 10566), AKR1B1 (EG: 231), ALB (EG: 213), ALDOA (EG: 226), ALDOC (EG: 230), AMBP (EG: 259), AMPD3 (EG: 272), AMPH (EG: 273), ANGPT1 (EG: 284), ANTXR2 (EG: 118429), ANXA2 (EG: 302), AP1B1 (EG: 162), AP1M1 (EG: 8907), AP2A1 (EG: 160), APC (EG: 324), APEH (EG: 327), APEX1 (EG: 328), APLP2 (EG: 334), APOA2 (EG: 336), APOA4 (EG: 337), APOC1 (EG: 341), APOC2 (EG: 344), APOC3 (EG: 345), APOD (EG: 347), APRT (EG: 353), AQP3 (EG: 360), AR (EG: 367), ARF1 (EG: 375), ARF2 (EG: 376), ARF3 (EG: 377), ARHGEF1 (EG: 9138), ARL3 (EG: 403), ARRB1 (EG: 408), ARRB2 (EG: 409), ARSA (EG: 410), ASCC3L1 (EG: 23020), ATF4 (EG: 468), ATP2A2 (EG: 488), ATP2B4 (EG: 493), ATP5B (EG: 506), ATP5D (EG: 513), ATP6V1E1 (EG: 529), BAG2 (EG: 9532), BAT1 (EG: 7919), BBC3 (EG: 27113), BCAR3 (EG: 8412), BCL2L1 (EG: 598), BGN (EG: 633), BLMH (EG: 642), BTK (EG: 695), BTRC (EG: 8945), C1QBP (EG: 708), C4A (EG: 720), CACNA1H (EG: 8912), CALM2 (EG: 805), CALM3 (EG: 808), CAMK1 (EG: 8536), CAPZA1 (EG: 829), CAPZB (EG: 832), CASP7 (EG: 840), CASP9 (EG: 842), CAV1 (EG: 857), CBLB (EG: 868), CBR1 (EG: 873), CCDC59 (EG: 29080), CCNA1 (EG: 8900), CCNB1 (EG: 891), CCS (EG: 9973), CD200 (EG: 4345), CD22 (EG: 933), CD2AP (EG: 23607), CD3E (EG: 916), CD4 (EG: 920), CD46 (EG: 4179), CD47 (EG: 961), CD48 (EG: 962), CD5 (EG: 921), CD59 (EG: 966), CD74 (EG: 972), CD9 (EG: 928), CD93 (EG: 22918), CDH11 (EG: 1009), CDH15 (EG: 1013), CDH3 (EG: 1001), CDH6 (EG: 1004), CDK4 (EG: 1019), CDKN2A (EG: 1029), CEBPB (EG: 1051), CFB (EG: 629), CFD (EG: 1675), CFH (EG: 3075), CFTR (EG: 1080), CHRNA7 (EG: 1139), CHUK (EG: 1147), CITED1 (EG: 4435), CKB (EG: 1152), CLIC1 (EG: 1192), CLIC4 (EG: 25932), CLIC6 (EG: 54102), CLU (EG: 1191), CNTNAP3 (EG: 79937), CNTNAP4 (EG: 85445), COL1A1 (EG: 1277), COL1A2 (EG: 1278), COL4A1 (EG: 1282), COMT (EG: 1312), COPA (EG: 1314), COPB2 (EG: 9276), COPE (EG: 11316), COPG (EG: 22820), CREBBP (EG: 1387), CRK (EG: 1398), CRKL (EG: 1399), CRYZ (EG: 1429), CSE1L (EG: 1434), CSF1R (EG: 1436), CSK (EG: 1445), CSNK1D (EG: 1453), CSNK1E

TABLE 3-continued

Class 3 - Potential partners of Class 1 genes:

(EG: 1454), CST3 (EG: 1471), CTAGE5 (EG: 4253), CTGF (EG: 1490), CTNNA1
(EG: 1495), CUTA (EG: 51596), CYCS (EG: 54205), DAB2 (EG: 1601), DAG1
(EG: 1605), DAXX (EG: 1616), DCD (EG: 117159), DCTN1 (EG: 1639), DCUN1D1
(EG: 54165), DDEF1 (EG: 50807), DDEF2 (EG: 8853), DDOST (EG: 1650), DDR1
(EG: 780), DDX21 (EG: 9188), DFFA (EG: 1676), DGKD (EG: 8527), DLG1 (EG: 1739),
DMD (EG: 1756), DMP1 (EG: 1758), DNAJA1 (EG: 3301), DNAJA3 (EG: 9093),
DNAJB2 (EG: 3300), DNM2 (EG: 1785), DOCK1 (EG: 1793), DOK1 (EG: 1796),
DPYSL2 (EG: 1808), DSP (EG: 1832), DUSP3 (EG: 1845), DYNLL1 (EG: 8655), E2F1
(EG: 1869), EEF1A2 (EG: 1917), EEF1D (EG: 1936), EEF1G (EG: 1937), EIF2A
(EG: 83939), EIF4G1 (EG: 1981), ELF1 (EG: 1997), ELF3 (EG: 1999), EP300
(EG: 2033), EPB41 (EG: 2035), EPRS (EG: 2058), EPS8 (EG: 2059), ERBB2 (EG: 2064),
ERBB2IP (EG: 55914), ERP29 (EG: 10961), ESD (EG: 2098), ESR1 (EG: 2099), ETS1
(EG: 2113), F7 (EG: 2155), FADD (EG: 8772), FGA (EG: 2243), FHL1 (EG: 2273),
FHL2 (EG: 2274), FHOD1 (EG: 29109), FLNC (EG: 2318), FLOT1 (EG: 10211), FLOT2
(EG: 2319), FN1 (EG: 2335), FOS (EG: 2353), FOXM1 (EG: 2305), FPR1 (EG: 2357),
FUBP1 (EG: 8880), GAB1 (EG: 2549), GABARAPL2 (EG: 11345), GANAB
(EG: 23193), GAPDH (EG: 2597), GATA1 (EG: 2623), GC (EG: 2638), GCLM
(EG: 2730), GCN1L1 (EG: 10985), GDI2 (EG: 2665), GFI1B (EG: 8328), GJB1
(EG: 2705), GM2A (EG: 2760), GNA11 (EG: 2767), GNAQ (EG: 2776), GNAS
(EG: 2778), GNAZ (EG: 2781), GNB1 (EG: 2782), GNPDA1 (EG: 10007), GOLGA4
(EG: 2803), GP6 (EG: 51206), GPC1 (EG: 2817), GPRASP1 (EG: 9737), GRAP2
(EG: 9402), GRB2 (EG: 2885), GRIN1 (EG: 2902), GRIN2A (EG: 2903), GRM1
(EG: 2911), GSN (EG: 2934), GSTM3 (EG: 2947), GTF2I (EG: 2969), HABP2
(EG: 3026), HBEGF (EG: 1839), HCK (EG: 3055), HCLS1 (EG: 3059), HDAC1
(EG: 3065), HDAC2 (EG: 3066), HIST1H1E (EG: 3008), HLA-A (EG: 3105), HMGA1
(EG: 3159), HMGB1 (EG: 3146), HMMR (EG: 3161), HMOX2 (EG: 3163), HNF4A
(EG: 3172), HNRPF (EG: 3185), HNRPH1 (EG: 3187), HNRPM (EG: 4670), HPRT1
(EG: 3251), HPX (EG: 3263), HRAS (EG: 3265), HSP90AA1 (EG: 3320), HSP90AB1
(EG: 3326), HSPA1A (EG: 3303), HSPA1L (EG: 3305), HSPA6 (EG: 3310), HSPA8
(EG: 3312), HSPB1 (EG: 3315), HSPD1 (EG: 3329), HSPE1 (EG: 3336), HSPG2
(EG: 3339), HTR2C (EG: 3358), ID2 (EG: 3398), IFIH1 (EG: 64135), IFNG (EG: 3458),
IGF1 (EG: 3479), IGFBP3 (EG: 3486), IGHG1 (EG: 3500), IKBKB (EG: 3551), IKBKE
(EG: 9641), IKBKG (EG: 8517), IL2RA (EG: 3559), ILK (EG: 3611), INADL
(EG: 10207), IRF2 (EG: 3660), IRS1 (EG: 3667), ITGA2 (EG: 3673), ITGA3 (EG: 3675),
ITGA4 (EG: 3676), ITGAV (EG: 3685), ITGB3 (EG: 3690), ITIH1 (EG: 3697), ITPR3
(EG: 3710), JAK2 (EG: 3717), JUP (EG: 3728), KCNJ2 (EG: 3759), KCTD12
(EG: 115207), KIAA0152 (EG: 9761), KIAA1217 (EG: 56243), KIF13B (EG: 23303),
KIF17 (EG: 57576), KIF5C (EG: 3800), KLF3 (EG: 51274), KPNA1 (EG: 3836), KPNA2
(EG: 3838), KPNA3 (EG: 3839), KPNA4 (EG: 3840), KPNB1 (EG: 3837), KRT1
(EG: 3848), KRT10 (EG: 3858), KRT13 (EG: 3860), KRT16 (EG: 3868), KRT17
(EG: 3872), KRT18 (EG: 3875), KRT5 (EG: 3852), KRT6A (EG: 3853), KRT6B
(EG: 3854), KRT8 (EG: 3856), KRT9 (EG: 3857), L1CAM (EG: 3897), LAMA5
(EG: 3911), LAT (EG: 27040), LCK (EG: 3932), LETM1 (EG: 3954), LGALS8
(EG: 3964), LIMS1 (EG: 3987), LOC643751 (EG: 643751), LRRFIP2 (EG: 9209),
LTA4H (EG: 4048), LYL1 (EG: 4066), LYZ (EG: 4069), MADCAM1 (EG: 8174),
MAML1 (EG: 9794), MAP1A (EG: 4130), MAP2K2 (EG: 5605), MAP3K1 (EG: 4214),
MAP3K14 (EG: 9020), MAP3K3 (EG: 4215), MAP3K7IP2 (EG: 23118), MAP3K8
(EG: 1326), MAP4K3 (EG: 8491), MAPK10 (EG: 5602), MAPK9 (EG: 5601), MAPRE1
(EG: 22919), MARK2 (EG: 2011), MATR3 (EG: 9782), MAX (EG: 4149), MCF2
(EG: 4168), MCM4 (EG: 4173), MCM6 (EG: 4175), MCM7 (EG: 4176), MDH2
(EG: 4191), MDM2 (EG: 4193), MEP1A (EG: 4224), MICAL1 (EG: 64780), MIF
(EG: 4282), MMP14 (EG: 4323), MPG (EG: 4350), MRCL3 (EG: 10627), MSH2
(EG: 4436), MSH6 (EG: 2956), MTHFD1 (EG: 4522), MTPN (EG: 136319), MUC2
(EG: 4583), MYB (EG: 4602), MYH10 (EG: 4628), MYH4 (EG: 4622), MYH9
(EG: 4627), MYL4 (EG: 4635), MYL6 (EG: 4637), NARG1 (EG: 80155), NBPF3
(EG: 84224), NCF1 (EG: 4687), NCKIPSD (EG: 51517), NCOA3 (EG: 8202), NCOR1
(EG: 9611), NCOR2 (EG: 9612), NEDD8 (EG: 4738), NFKB2 (EG: 4791), NFKBIA
(EG: 4792), NFKBIB (EG: 4793), NFKBIE (EG: 4794), NID1 (EG: 4811), NKX3-1
(EG: 4824), NOTCH4 (EG: 4855), NP (EG: 4860), NPEPPS (EG: 9520), NPR1
(EG: 4881), NSF (EG: 4905), NTRK3 (EG: 4916), NUDC (EG: 10726), NUDT5
(EG: 11164), OSM (EG: 5008), P4HB (EG: 5034), PACSIN3 (EG: 29763), PAFAH1B1
(EG: 5048), PAFAH1B2 (EG: 5049), PAICS (EG: 10606), PAK2 (EG: 5062), PAM
(EG: 5066), PARD3 (EG: 56288), PARD6A (EG: 50855), PARP1 (EG: 142), PAWR
(EG: 5074), PCBD1 (EG: 5092), PCDH1 (EG: 5097), PCMT1 (EG: 5110), PCNA
(EG: 5111), PDCD10 (EG: 11235), PDCD5 (EG: 9141), PDCD6IP (EG: 10015), PDLIM7
(EG: 9260), PEA15 (EG: 8682), PECAM1 (EG: 5175), PEX19 (EG: 5824), PF4V1
(EG: 5197), PFAS (EG: 5198), PFDN2 (EG: 5202), PFKM (EG: 5213), PGF (EG: 5228),
PGRMC1 (EG: 10857), PHC3 (EG: 80012), PIGR (EG: 5284), PIK3CD (EG: 5293),
PIK3CG (EG: 5294), PIK3R2 (EG: 5296), PIN1 (EG: 5300), PKD1 (EG: 5310), PKN1
(EG: 5585), PKN2 (EG: 5586), PLCG1 (EG: 5335), PLCG2 (EG: 5336), PLTP
(EG: 5360), PPIB (EG: 5479), PPM1B (EG: 5495), PPP1R12C (EG: 54776), PPP2CB
(EG: 5516), PPP2R1A (EG: 5518), PPP4C (EG: 5531), PRKAR2A (EG: 5576),
PRKAR2B (EG: 5577), PRKCB1 (EG: 5579), PRKCE (EG: 5581), PRKDC (EG: 5591),
PRSS1 (EG: 5644), PRSS3 (EG: 5646), PSMA1 (EG: 5682), PSMA2 (EG: 5683),
PSMA3 (EG: 5684), PSMA6 (EG: 5687), PSMA7 (EG: 5688), PSMB3 (EG: 5691),
PSMD13 (EG: 5719), PSMD14 (EG: 10213), PSMD2 (EG: 5708), PSMD8 (EG: 5714),
PTGES3 (EG: 10728), PTPN1 (EG: 5770), PTPN12 (EG: 5782), PTPN3 (EG: 5774),
PTPRA (EG: 5786), PTPRC (EG: 5788), PTPRD (EG: 5789), PTPRS (EG: 5802), PUS7

TABLE 3-continued

Class 3 - Potential partners of Class 1 genes:

(EG: 54517), RAB10 (EG: 10890), RAB13 (EG: 5872), RAB1B (EG: 81876), RAB37
(EG: 326624), RAB3A (EG: 5864), RAB3C (EG: 115827), RAB3D (EG: 9545), RAB8A
(EG: 4218), RAD23A (EG: 5886), RAF1 (EG: 5894), RANBP2 (EG: 5903), RANBP9
(EG: 10048), RAP2B (EG: 5912), RAPGEF1 (EG: 2889), RARG (EG: 5916), RASA1
(EG: 5921), RASA2 (EG: 5922), RASAL2 (EG: 9462), RBBP4 (EG: 5928), RELA
(EG: 5970), RELB (EG: 5971), REXO2 (EG: 25996), RGS12 (EG: 6002), RGS16
(EG: 6004), RGS2 (EG: 5997), RGS4 (EG: 5999), RHAG (EG: 6005), RHOB (EG: 388),
RHOC (EG: 389), RHOQ (EG: 23433), RHPN2 (EG: 85415), RIN2 (EG: 54453), RP4-
691N24.1 (EG: 22981), RPGR (EG: 6103), RPL35 (EG: 11224), RPS14 (EG: 6208),
RPS27A (EG: 6233), RPS3A (EG: 6189), RRM1 (EG: 6240), RUNX1 (EG: 861),
RUNX3 (EG: 864), RUVBL1 (EG: 8607), RUVBL2 (EG: 10856), RXRA (EG: 6256),
SAA1 (EG: 6288), SACS (EG: 26278), SCN5A (EG: 6331), SCYE1 (EG: 9255), SDC1
(EG: 6382), SDCBP (EG: 6386), SDHB (EG: 6390), SEC23B (EG: 10483), SEC63
(EG: 11231), SELE (EG: 6401), SELL (EG: 6402), SEPT2 (EG: 4735), SEPT5
(EG: 5413), SF3B14 (EG: 51639), SFN (EG: 2810), SFPQ (EG: 6421), SGOL2
(EG: 151246), SH2D1A (EG: 4068), SH3BGRL2 (EG: 83699), SH3GL3 (EG: 6457),
SH3GLB1 (EG: 51100), SHC1 (EG: 6464), SHC2 (EG: 25759), SHC3 (EG: 53358),
SIN3B (EG: 23309), SLA2 (EG: 84174), SLC1A5 (EG: 6510), SLC3A2 (EG: 6520),
SLC4A1 (EG: 6521), SMAD1 (EG: 4086), SMAD2 (EG: 4087), SMARCA4 (EG: 6597),
SMARCB1 (EG: 6598), SMARCC1 (EG: 6599), SMARCD2 (EG: 6603), SNAP23
(EG: 8773), SNX2 (EG: 6643), SNX3 (EG: 8724), SNX4 (EG: 8723), SOCS3 (EG: 9021),
SORBS3 (EG: 10174), SORL1 (EG: 6653), SOS1 (EG: 6654), SP1 (EG: 6667), SP3
(EG: 6670), SPAG9 (EG: 9043), SPAST (EG: 6683), SPI1 (EG: 6688), SPTAN1
(EG: 6709), SPTBN1 (EG: 6711), SRI (EG: 6717), SSTR5 (EG: 6755), ST13 (EG: 6767),
STARD13 (EG: 90627), STAT6 (EG: 6778), STK24 (EG: 8428), STOML2 (EG: 30968),
STX12 (EG: 23673), STX18 (EG: 53407), SVIL (EG: 6840), SYK (EG: 6850), SYMPK
(EG: 8189), TACSTD1 (EG: 4072), TAGLN2 (EG: 8407), TARS (EG: 6897), TAT
(EG: 6898), TBCA (EG: 6902), TBXA2R (EG: 6915), TCF3 (EG: 6929), TEC (EG: 7006),
TEK (EG: 7010), TFRC (EG: 7037), TGFBI (EG: 7045), TGM2 (EG: 7052), THBS3
(EG: 7059), TIMP1 (EG: 7076), TJAP1 (EG: 93643), TJP1 (EG: 7082), TKT (EG: 7086),
TLN2 (EG: 83660), TMED2 (EG: 10959), TMOD3 (EG: 29766), TNIP2 (EG: 79155),
TNK2 (EG: 10188), TP73 (EG: 7161), TPM2 (EG: 7169), TPP2 (EG: 7174), TPR
(EG: 7175), TRADD (EG: 8717), TRAF2 (EG: 7186), TRIM29 (EG: 23650), TRIP4
(EG: 9325), TRIP6 (EG: 7205), TSC22D1 (EG: 8848), TSC22D3 (EG: 1831), TSHR
(EG: 7253), TSN (EG: 7247), TTN (EG: 7273), TTR (EG: 7276), TUBA8 (EG: 51807),
TUBB (EG: 203068), TUBB6 (EG: 84617), TUFM (EG: 7284), TXN (EG: 7295),
TXNDC4 (EG: 23071), TYRO3 (EG: 7301), UBA2 (EG: 10054), UBB (EG: 7314),
UBE2G2 (EG: 7327), UBE2I (EG: 7329), UBE2L3 (EG: 7332), UBE2L6 (EG: 9246),
UCHL1 (EG: 7345), UGCGL1 (EG: 56886), UMPS (EG: 7372), UNC119 (EG: 9094),
UNC5CL (EG: 222643), UTRN (EG: 7402), VASP (EG: 7408), VAV2 (EG: 7410), VCP
(EG: 7415), VDAC1 (EG: 7416), VIM (EG: 7431), VLDLR (EG: 7436), WAS
(EG: 7454), YWHAB (EG: 7529), YWHAE (EG: 7531), YWHAG (EG: 7532), YWHAH
(EG: 7533), YWHAQ (EG: 10971), YWHAZ (EG: 7534), ZAP70 (EG: 7535), ZYX
(EG: 7791).

The above groups of genes (or the corresponding RNAs, proteins, ligands, associated SNPs or metabolites associated with the activity of proteins encoded by these genes) represent valuable biomarkers which may be used, alone or in various combinations, to diagnose AD or related disorders.

In a preferred embodiment, a set of biomarkers of the invention comprises at least two biomarkers. In other embodiments, the set of biomarkers of the invention comprises at least 3, 4, 5, 6, 7 or more biomarkers.

In the most preferred embodiment, the set of biomarkers according to the invention comprises at least two proteins or RNAs encoded by the genes selected from the group consisting of: APBA1, ATG7, BECN1, CD44, CDH2, COL18A1, ERBB4, F3, FLNA, FYN, GRIN2B, IL20, ITPR1, LRP8, MTOR, NPPC, NRP1, PDGFC, ROBO1, SEMA3E, TGFB1, THBS1, VEGFR1 and WWOX. In other embodiments, a set of biomarkers of the invention comprises at least 3, 4, 5, 6, 7 or more proteins or RNAs encoded by the genes listed above.

A set of target biomarkers according to the invention may also comprise one or more biomarkers as listed above in combination with at least one additional biomarker. Typically, such additional biomarkers are selected from disease associated SNPs, proteins, RNAs, metabolites, lipids or glucids.

In a preferred embodiment, one or more additional biomarkers are selected from proteins or RNAs encoded by the genes selected from: A2M, ACHE, ALDH2, ANXA1, APOA1, ATP2A3, CASK, CASP8, CDH1, CDH5, CDKN1A, CHAT, CTNND2, DOCK3, EDN1, F13A1, FGF2, FLNB, GABRB2, ITGA1, LAMA1, LAMA3, LEPR, LRP1, MAP2, MMP9, NFATC2, NOS3, NOTCH3, NPPB, PDGFA, PDGFB, PIK3CB, PLAU, PLXDC2, PLXNA2, PRKG1, PRNP, PTK2, RYR2, SEMA5A, SERPINA6, SERPINB2, SERPIND1, STAT3, THBS2, TNF, TP53, TRPC4, TSC1 and VEGFA.

In another preferred embodiment, one or more additional biomarkers are selected from proteins or RNAs encoded by the genes selected from: ABCC4, ACC2, ACTN1, ADAM12, ADRA1A, AKAP13, ALCAM, ANXA3, ARHGEF11, ARHGEF12, ATF3, ATM, ATP6V1C1, ATR, BAP1, BGLAP, BIN1, BRIP1, BSN, CACNA1D, CALCB, CDC42BPB, CDH12, CDH13, CHEK1, CHL1, CLTC, COL3A1, COPS7B, CSF1, CSH1, CSNK1A1, CTNNA2, CUL1, CYP11A1, DAAM1, DGKZ, DLG3, DOCK2, EGF, EGFR, EPB41L2, ERC1, F2, FAS, FER1L3, FES, FKBP1A, FSTL5, GFRA3, GFRA4, GH1, GRIP1, GUCY2D, HGF, HIPK1, HMBOX1, HRG, HSP90B1, HSPA5, HYOU1, IGF2, IL16, IL6ST, IL8, INS, IPPK, IQGAP1, IQGAP2, ITGA9, JAK1, LEP, LETMD1, LIFR, LRP2, LRP6, LTBP1, MAD1L1, MAML3, MMP2, MMP3, MSR1, MUC1, MYO10, NCAM1, NCK1, NGF, NISCH, NOS1, NOTCH2, NPPA, NRIP1, NTF3, OPRM1, PCAF, PCLO, PDE3A, PDE5A, PFKP, PRLR, PIK3CA, PLA2G2A, PLAT, PLG, PRL, PRLR, PSAP, PSD3, PTGS2, PTK2B, PTPRF, PTPRG, PTPRM, RELN, RET, RIMS2, ROCK1, RPS6KA1, RPS6KA2, RPS6 KB1, SCN9A, SERPINA5, SERPINC1, SERPINE1, SERPINE2, SNAP25, SPP1, SREBF2, STAT5B, SV2B, TIMP2, TNFSF11, TRIO, TSC2, UBE3A, VCL, VIL2, WASPIP, XDH and ZFHX1B.

In another embodiment, the additional biomarker(s) is/are selected from metabolites of:

cholesterol metabolic pathway, preferably including cholesterol, cholesterol ester, pregnenolone, allopregnanolone, cholest-5-ene-3β,26-diol, dehydroepiandrosterone and dehydroepiandrosterone sulfate, or combination thereof; and/or folate metabolic pathway, preferably including 5-methyltetrahydrofolate, folic acid, s-adenosyl methionine, homocysteine and tetrahydrofolate, or combination thereof; and/or phosphatidic acid metabolic pathway, preferably including phosphatidic acid, lysophosphatidic acid, phosphatidylcholine, phosphatidylethanolamine, phosphatidylglycerol, phosphatidylglycerophosphate, or combination thereof; and/or sphingosine metabolic pathway, preferably including sphingosine-1-phosphate, sphingosine and C2-ceramide, or combination thereof; and/or terpenoid metabolic pathway, preferably including mevalonate, geranyl diphosphate, geranylgeranyl diphosphate and farnesyl diphosphate.

In a particular embodiment, the biomarker(s) of the invention is/are a SNP or a combination of SNPs for the genes listed above, or for other genes involved:

in synapse biology, for example: ADARB2, AKAP11, ATG5, BDNF, CAMK2D, CDH18, CDH22, CDH8, CDH9, CITRON, CNGB3, DLG2, DLGAP1, DOCK4, DOCK9, DPP6, EML1, FMN1, GRIA4, GRID1, GRID2, GRIK1, GRIK2, GRIK3, GRIK4, GRM7, GRM8, KCND2, LPHN2, MMP7, NAALAD2, NLGN1, NRCAM, NRG1, NRG3, NRG4, NRXN1, NRXN3, NTRK2, OPCML, P2RX4, PARK2, PVRL1, RASGRF2, SCAP2, SLC1A4, SLC6A20, SLC6A7, SNCA, SORBS2, YES1, ABL1, ADAM17, AKT1, CALM1, CBL, CDC42, CREB1, CTNNB1, DLG4, DLGAP2, DLGAP3, DLGAP4, GOPC, GRIA2, GRIA3, GRIN3A, GRIP2, GRM3, GRM5, GRM6, HOMER1, KCNIP1, KCNIP2, LYN, MAPK1, MAPK3, NGFR, NRAS, PIAS1, PICK1, PIK3R1, PIK3R4, PPP1CA, PPP3CA, PPP3CB, PPP3CC, PRKACA, PRKACB, PRKCA, RAP1A, RAP1B, RHOA, ROCK2, SRC, SUMO1, TBR1, UBE2A, YAP1, ABAT, APBA3, APBB1, B3GNTL1, CACNA1C, CACNA1E, CACNA2D1, CACNA2D3, CACNA2D4, CACNB2, CADPS2, CALN1, CAMK4, CAST1, CDKAL1, CNTN4, CSMD1, CUGBP2, DAPK1, DAPK2, DBC1, DISC1, DNER, DRD2, FGF12, FREQ, GABBR2, GABRA2, GABRB3, GABRG3, GLRA1, GLUD1, GUCY1B2, KCNJ6, KCNMA1, KYNU, NFKB1, NOS1AP, ODZ2, PDE11A, PDE4D, PICALM, PRKD3, RAB3B, RGS8, RIMS1, RPH3AL, SCN11A, SEC24D, SLC12A6, SLC1A1, SLC1A2, SLC1A3, SLC6A1, SLC6A18, SNPH, SNX9, STX2, STXBP6, SV2C, SYN3, SYT12, SYT2, UNC13C, VAMPS, ANKRA2, BACE1, CDC2, CDK5, CHRM1, CHRM3, CHRM4, CHRM5, CTNN, DNM1, ERC2, GUCY2C, GUCY2E, GUCY2F, GUCY2G, KCNMB1, LIN7A, LIN7B, LIN7C, NOVA1, PRKAA1, PRKAA2, PRKAB1, PRKAB2, PRKAG1, RPH3A, SCN1A, SCN1B, SH3GL2, SLC9A1, STX1A, STXBP1, SYNJ1, SYNJ2, SYTL4, UNC13B, VAMP2, WASF1, ALK, ANKS1A, ARHGAP18, ARHGAP26, CDC42EP3, CDH10, CDH4, DAB1, DCC, DEPDC2, DNM3, EFNA5, EPHA10, EPHA3, EPHA6, EPHB6, GIPC2, HEY2, KALRN, KTN1, NAV1, NBEA, NCK2, NGEF, NRP2, PAK6, PAK7, PCDH9, PLD2, PPFIA2, PPFIBP1, PPFIBP2, PPP1R12A, PTN, ROBO2, ROR1, ROR2, SDK1, SEMA3A, SEMA3C, SEMA7A, SLIT1, SORBS1, SRGAP3, ULK4, UNC5C, ABI1, ADORA2B, CASR, CRMP1, GDNF, GFRA1, GFRA2, GNA12, HTR1B, HTR1D, IQUB, MYL1, NOTCH1, NTN1, NTN3, PIP5K1A, PIP5K1B, RAC1, RBPJ, RGNEF, RHOG, SEMA4C, SIAH1; and/or in angiogenesis, for example: ADAMTS12, ADIPOQ, ANGPT2, ANK1, ARHGAP10, ARHGAP17, ARHGAP22, ARNT2, BAI3, BMP3A, CA10, CALCR, COL4A2, COL4A3BP, COMMD1, COMMD10, DBT, DRD2, EDNRA, EFNA5, EPHA3, FABP5, FBLN2, FOXO3A, GIPC2, GPC6, GULP1, HAPLN1, HAS2, HIF1A, HPSE2, IL18R1, IL20RA, IL20RB, ITGA11, LTBP2, MMP10, MMP7, NCK2, NEDD4, NEDD9, NFKB1, NR3C2, NRG1, NRP2, P2RY12, PAK6, PALLD, PARVA, PCSK5, PDE11A, PDE1A, PDE4D, PDGFRA, PPM1E, PTN, RPSA, SCHIP1, SEMA3A, SEMA3C, SEMA7A, SMAD4, SMYD3, SND1, SORBS2, SPOCK1, SPOCK3, STAB2, TGFBRAP1, TLL2, VAV3, VEGFR2, YES1, BCAR1, CD36, CDC42, CTNN, F2R, FOXO1, GUCY2C, GUCY2E, GUCY2F, GUCY2G, HYAL1, HYAL2, HYAL3, HYAL4, ITCH, ITGA6, ITGB1, MAPK1, MAPK3, MET, MME, NF2, P2RY1, PAK1, PDGFRB, PIK3R1, PIK3R4, PPARA, PXN, RAC1, RDX, RHOA, SMAD3, STAT5A, TGFBR1, TGFBR2, TGFBR3, TIAM1, VEGFB, VEGFC, VEZF1, ABCA1, ACADSB, ACOT11, ACOT7, ACOXL, AKAP2, ATP7B, AUH, BDH2, CAMK1D, CAMKK2, CNTFR, COLEC12, CS, CUBN, CYP19A1, CYP1B1, CYP7B1, DHCR7, DLD, EHHADH, ETFA, FTO, GABBR2, GLRX, HCRTR2, HSD17B12, LIPL3, ME1, ME2, MGLL, NCOA1, NFYB, OGDH, OSBPL10, OSBPL3, PC, RPS6KA5, SCARF2, SDHA, SLC22A4, SLC25A21, SOCS1, SRD5A1, TBXAS1, ACAT1, ADIPOR1, ADIPOR2, ADRB2, AKR1C2, CPT1A, CPT1B, EIF4E, EIF4EBP1, ESRRG, FDPS, HSD11B1, LDLR, NR1I2, NRAS, OPRS1, PPARG, PPARGC1B, PRKAA1, PRKAA2, PRKAB1, PRKAB2, PRKACA, PRKACB, PRKAG1, PTPN11, RHEB, RPS6KB2, RPTOR, SCARB1, SREBF1, STAR, STK11, THRA, THRB, TSPO, ADCY2, ADH5, AGPAT5, AGPAT7, ASAH1, ATIC, ATP10A, ATP10B, ATP10D, CDH8, CDH9, DGKB, DGKE, DGKG, DGKH, ENPP2, ENPP6, ENPP7, GATA3, GDF2, GNG12, MAT2B, MGST2, MTR, MTRR, PAFAH2, PIP5K2A, PISD, PITPNC1, PLA2R1, PLCB1, PLCL1, PLD2, PRIMA1, RALA, RALBP1, SCGB1A1, SGMS1, SGPP2, SHMT1, SNCA, ST14, THEM2, TRPS1, ADRBK1, CYSLTR1, CYSLTR2, DHFR, DRD5, EDG1, EDG2, EDG3, EDG4, EDG5, EDG6, EDG7, EDG8, GNAI2, GNAI3, GNAI1, GNAI2, GNAI3, GRK5, GRM5, LPIN1, LPIN2, LPIN3, MYCBP2, PCTP, PLA2G1B, PLA2G4A, PLA2G5, PLA2G6, PLD1, PPAP2A, PPAP2B, PPAP2C, PRKCD, ALX4, CDON, CST5, GDF10, HIVEP2, NOG, OSTN, ROR2, RUNX2, SOX5, SOX9, TNFRSF11B, BMP2, FGF4, FZD2, HOXD13, MAPK8, SHH, SMAD5, SOX6, TNFRSF11A, VDR, WNT5A; and/or in cell stress response, for example: ACYP2, ATP2B1, ATP2B2, ATXN1, DGKB, DGKE, DGKG, DGKH, ITPR2, PDE11A, PDE4D, PLCB1, PLEKHA6, SILL SLC8A1, TRPM3, ATP1A1, CHRM1, CHRM3, CHRM4, CHRM5, DNAJB9, FKBP1B, GUCY2C, GUCY2E, GUCY2F, GUCY2G, IMPDH1, IMPDH2, IRF1, MSN, PLN, PPP3CA, PPP3CB, PPP3CC, PRKCA, RDX, RYR3, SCN1A, SCN1B, SLC8A2, SLC9A3R1, SLC9A3R2, SLN, TRPC3, TRPC5, AKAP11, APBA2BP, APBB1, APPBP2, BCL2, CDK5RAP2, CDKAL1, CHMP5, CHRM2, DAB1, DNAJB11, DRD2, ELAVL2, ENAH, FGF14, FGF5, FMN1, FRS2, FZD3, GAB2, GLI2, GPC5, INSR, HAS2, HECW1, HTR1A, IDE, IGF1R, IGF2BP1, INPP4A, INPP4B, KREMEN1, NEDD4, NOG, NOS1AP, PARK2, PDE6D, PIK3C2G, PVRL1, ROR2, SFRP4, SNCA, SNCAIP, SORCS1, SORCS2, TFCP2, VANGL2, VPS13B, WIF1, ADRB2, ADRBK1, AKT1, BACE1, BAX, CCNE1, CDK5, CTNNB1, DVL1, FGFR1, FZD2, GNB2L1, GPR37, GRK5, GSK3B, ITGB1, MAOA, MAOB, MAPK1, MAPK3, MAPK8, MLLT4, MME, PRKAA1, PRKAA2, PRKAB1, PRKAB2, PRKACA, PRKACB, PRKAG1, RAC1, SRC, WNT1, WNT5A, ABCC9, ACCN1, ACCN2, ATF7, ATG10, ATG5, BCL2L14, BCL3, BRE, BR13BP, CDK6, COMMD1, COMMD10, COPS7A, DAPK1, DAPK2, DCC, EYA2, FBXW8, FHIT, FOXO3A, GNPTAB, HBG2, HIPK2, HK2, HMOX1, JARID1B, MBNL2, MCC1, MCPH1, MDM1, NEDD9, NFKB1, NOX3, NRP2, NUDT1, NUDT13, NUDT3, PIK3C3, PML, PPM1D, RBBP8, RTN1, SEMA3C, SH3BP5, SLC24A3, SORBS2, SQSTM1, TNFAIP3, UNC5C, VDAC2, YES1, ALOX12, ATG12, BAD, BAK1, BCAR1, CD36, GADD45A, GADD45B, GADD45G, HSPA4L, KCNJ11, KCNJ8, MAPK12, MLH1, NCF2, NOX1, NOX4, NTN1, PAK1, PIK3R4, SEMA4C, TNFRSF11A, TP63, TRAF6, CASP3.

An object of this invention is a method for detecting the presence or risk of AD or a related disorder in a mammal, or for aiding in the diagnosis and sub-classification of AD and related disorders, the method comprising determining the (relative) amount or the presence, absence or alteration of a target biomarker in a sample from the subject, wherein said amount or alteration is indicative of the presence, risk, progression or severity of said disease, and wherein said biomarker is selected from a protein, RNA, metabolite, lipid or glucid involved in synapse biology, angiogenesis or cellular stress response.

An object of the invention thus resides in a method for detecting (in vitro or ex vivo) the presence of or risk of developing AD or a related disorder in a mammal, comprising the determination of the presence, in a biological sample of the mammal of an alteration in one or more genes as listed in one of groups 1-3 above, or a corresponding RNA or protein, the presence of such an alteration being indicative of the presence of or risk of developing AD in said mammal.

Another object of this invention is a method for predicting and/or assessing the responsiveness of a subject to a treatment against AD and related disorders or the efficacy of such a treatment in a subject, the method comprising determining the (relative) amount or the presence, absence or alteration of a target biomarker in a sample from the subject, wherein said amount or alteration is indicative of the responsiveness of said subject or of the efficacy of the treatment, and wherein said biomarker is selected from a protein, RNA, metabolite, lipid or glucid involved in synapse biology, angiogenesis or cellular stress response.

Another object of the invention relates to a method to evaluate or follow the response to a treatment for AD in a subject, the method comprising a step of measuring the expression of one or more genes as listed in one of groups 1-3 above, or a corresponding RNA or protein, before and/or during the treatment, and a comparison of the expression thus measured with that measured at a former stage of the treatment or before treatment.

Another object of the invention relates to an improvement in methods of treating AD or related disorders, the improvement consisting in measuring the expression of one or, preferably, several genes as listed in one of groups 1-3 above, or a corresponding RNA or protein, before and/or during the treatment. The measurement of the expression makes it possible to adapt the treatment according to the evolution of pathology and/or efficacy of the treatment.

In a preferred embodiment, the method of the invention comprises the determination of the presence (or of the absence or the quantity (relative)), in a biological sample of the mammal, of at least 5 selected distinct molecules target among those above, preferably of at least 10.

An alteration in a gene or ARN or protein indicates, within the meaning of the invention, any alteration or deregulation of the expression of said gene, RNA or protein, at the transcriptional and/or translational level, as well as any alteration in the structure of the encoded protein(s) (appearance or disappearance of variants such as truncated, mutated or spliced variants).

Detecting an alteration in a gene or RNA expression or structure may be performed using a variety of techniques known per se in the art. These include, without limitation, Northern Blot, selective hybridization using e.g., nucleic acid arrays, nucleic acid amplification using e.g., RT-PCR, or quantitative PCR, Transcription-Mediated Amplification (TMA), Strand displacement Amplification (SDA), Amplification using Allele specific Oligonucleotide (ASO), Southern blot, conformational analysis SSCA, in situ hybridization (e.g., FISH), etc. If appropriate, the quantity/nature of nucleic acid detected can be compared with a reference value, for example a median or average value observed among control patients (e.g., not afflicted with AD), or with a value measured in parallel in a control sample.

According to a preferred embodiment, the method comprises the detection of the presence or absence or (relative) quantity of a nucleic acid sequence of a gene of a group of genes as listed above by selective hybridization or selective amplification.

Selective hybridization is typically carried out by using nucleic probes, preferably immobilized on a support, such as a solid or semi-solid support having at least a surface allowing the immobilization of nucleic probes. Such supports are for example glass slides, membranes, filters, columns, etc., which can be made out of any compatible material, like glass, silica, plastic, fiber, metal, polymer, etc. Nucleic acid probes can be made out of any nucleic acid (e.g., DNA, RNA, PNA, etc), preferably single stranded. Probes typically comprise from 5 to 400 bases, preferably from 8 to 200, more preferentially less than 100. Probes are specific for and complementary to at least a portion of a gene or RNA sequence as listed above, thereby allowing specific detection thereof through hybridization.

Hybridization can be performed under conventional (e.g., low, medium or high) stringency conditions, known to the skilled artisan, as disclosed e.g., in Sambrook, Fritsch, Maniatis (1989) Molecular Cloning, Cold Spring Harbor Laboratory Near.

A particular object of the invention thus resides in a method for detecting the presence of or the risk to develop AD or a related disorder in a mammal, or to evaluate the responsiveness of a subject or the efficacy of a treatment against AD, the method comprising contacting, under conditions allowing a hybridization between complementary sequences, nucleic acids from a sample of the mammal and a specific set of probes as defined above, to obtain a hybridization profile, the hybridization profile being characteristic of the presence or the risk to develop AD in this mammal, or of the responsiveness or efficacy of the treatment. The hybridization profile can be compared with one or more reference profiles, in particular a reference profile characteristic of healthy subjects and/or subjects afflicted with AD, the comparison allowing to determine the probability or the risk for the patient to have or develop AD.

Selective amplification is preferably carried out by using a primer or a pair of primers allowing the amplification of all or part of a target gene or RNA as disclosed above in a sample from the subject. The primer is typically specific for and complementary to a portion of the sequence of a target gene or RNA as defined above, and is generally a single stranded nucleic acid of between 5 and 50 bases in length, preferably between 5 and 30.

Another particular object of the invention thus resides in a method for detecting the presence or the risk of developing AD in a mammal, comprising contacting, under conditions allowing amplification to occur, nucleic acids from a sample of the mammal and a primer or set of primers as defined above to obtain an amplification profile, said profile being characteristic of the presence or risk of developing AD in said mammal.

In another embodiment, the method comprises the determination of the presence or (relative) quantity of a polypeptide encoded by a gene or RNA as defined above. Such determination can be made by various techniques known per se in the art, such as by means of a specific ligand, for example an antibody or a fragment or derivative thereof (e.g., Fab, Fab', CDR, ScFv, etc). The ligand is typically immobilized on a support, such as disclosed above. Techniques for detecting the formation of an immune complex include ELISA, RIA, etc. If appropriate, the detected amount of polypeptide can be compared to a reference value, for example a median or average value observed among control patients, or to a value measured in parallel in a control sample.

The method of the invention is applicable to any biological sample of the mammal to be tested, in particular any sample comprising nucleic acids or polypeptides. Examples of such samples include blood, plasma, serum, cerebrospinal fluid, saliva, urine, feces, cellular extracts, tissue biopsy, etc. The sample can be obtained by any technique known per se in the art, for example by collection using e.g., non invasive techniques, or from collections or banks of samples, etc. The sample can in addition be pretreated to facilitate the accessibility of the target molecules, for example by lysis (mechanical, chemical, enzymatic, etc), purification, centrifugation, separation, etc.

The invention is applicable to any mammal, preferably to human beings.

Methods of Identification of New Markers and Quantitation of Biomarkers

The present invention allows the detection of biomarkers of cerebral injury in biological fluids. The detection assays will be described below.

Those assays will include competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, fluorescent immunoassays and the like. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation consists in lysing cells with RIPA (RadioImmunoPrecipitation Assay) buffer that gives low background (50 mM Tris HCl pH 8, 150 mM NaCl, 1% NP-40, 0.1% SDS). As soon as lysis occurs, proteolysis, dephosphorylation and denaturation begin. These events can be slowed down tremendously if samples are kept on ice or at 4° C. at all times and appropriate inhibitors are added fresh to the lysis buffer. Two of the most commonly used protease inhibitors for IP are PMSF (50 ug/ml), and aprotinin (1 ug/ml). The sample is then incubated with the antibody for 1 hour to overnight at 4° C., preferably under agitation. Meanwhile the Sepharose beads are prepared. If using a monoclonal antibody choose protein G-coupled Sepharose beads, if using a polyclonal antibody protein A-coupled Sepharose beads are usually suitable. 70-100 µl of the beads are added to each sample, always kept on ice. The lysate-beads mixture is then incubated at 4° C. under rotary agitation for 4 hours. When the incubation time is over, tubes are centrifuged, the supernatant is removed and the beads are washed in lysis buffer three times (each time centrifuging at 4° C. and removing the supernatant). Finally, the last supernatant is removed and 25-50 µl of 2× loading buffer are added. The mixture is then boiled at 95-100° C. for 5 minutes to denature the protein and separate it from the protein-A/G beads, centrifuged and the supernatant contains the protein. The samples can be run on a Western Blot for further analysis.

Western Blot analysis consists in determining relative amounts of the protein of interest present in different samples. Proteins are separated by gel electrophoresis, usually SDS-polyacrylamide gel (also known as SDS-PAGE). Peptides are transferred to a sheet of special blotting paper called nitrocellulose: Place a nitrocellulose membrane on the gel and, using electrophoresis, drive the protein (polypeptide) bands onto the nitrocellulose membrane. This gives a nitrocellulose membrane that is imprinted with the same protein bands as the gel. The proteins retain the same pattern of separation they had on the gel. The blot is incubated with a generic protein (such as milk proteins) to bind to any remaining sticky places on the nitrocellulose. An antibody is then added to the solution which is able to bind to its specific protein. Primary antibody is incubated the nitrocellulose membrane, to form an antibody-protein complex with the protein of interest. The secondary antibody is then incubated with the nitrocellulose membrane. This antibody is an antibody-enzyme conjugate (e.g. alkaline phosphatase or horseradish peroxidase) directed against the primary. The location of the antibody is revealed by incubating it with a colorless substrate that the attached enzyme converts to a colored product that can be seen and photographed.

ELISAs (Enzyme Linked ImmunoSorbent Assay) consists in measuring the amount of antigen between two layers of antibodies. The antigens to be measured must contain at least two antigenic sites, capable to bind to two antibodies acting in the sandwich. So sandwich assays are restricted to the quantization of multivalent antigens such as proteins or polysaccharides. The principle of ELISA technique is the immobilization of capture antibody, followed by binding of antigen to immobilized antibody, binding of second antibody, linked to an enzyme, to bound antigen (formation of immune complex) and finally detection of immune complex using appropriate enzyme substrate. Although many different types of enzymes have been used for detection, horse radish peroxidase (HRP) and alkaline phosphatase (ALP) are the two widely used enzymes employed in ELISA assay.

It is important to consider the fact that some biological materials have high levels of endogenous enzyme activity (such as high ALP in alveolar cells, high peroxidase in red blood cells) and this may result in non-specific signal. When necessary, an additional blocking treatment with levamisol (for ALP) or with 0.3% solution of H2O2 in methanol (for peroxidase) is performed.

Identification and Quantitative Analysis of Biomarkers

Biological samples are taken from healthy volunteers (controls), similar in age, gender, physical condition to patients with cerebral injury. The comparisons of these biological samples allow to identify specific biomarkers of cerebral injury (as defined above).

Biological samples have to be processed for analysis such as chromatography (size exclusion, ion exchange, heparin affinity, sequential extraction, gel electrophoresis). There are many ways to reduce the complexity of a sample based on the binding properties of the proteins in the sample, or the characteristics of the proteins in the sample. Splitting and classifying samples will then favour suitable detection of biomarkers.

Exclusion chromatography might be used to split up a sample according to the size of proteins. For small biological samples, preferably a size selection spin column is used. In general, the first fraction that is eluted from the column ("fraction 1") has the highest percentage of high molecular weight proteins; fraction 2 has a lower percentage of high molecular weight proteins; fraction 3 has even a lower percentage of high molecular weight proteins; fraction 4 has the lowest amount of large proteins and so on. Each fraction can then be analyzed by immunoassays, gas phase ion spectrometry, and the like, for the detection of markers.

A sample can be split up by ion exchange chromatography that allows separation of the proteins according to their charge characteristics. For example, a biological sample can be processed in a Q anion-exchange resin (e.g., Q HyperD F, Biosepra) that will sequentially produce serial eluents having different pH. Anion exchange chromatography allows separation of the most negatively charged biomarkers: eluent having a basic pH is likely to be weakly negatively charged, whereas a fraction having a low pH is strongly negatively charged.

A sample can also be split up by heparin chromatography on the basis of affinity interaction with heparin and charge characteristics. Heparin, a sulfated mucopolysaccharide, will bind markers with positively charged moieties. Thus a sample can be sequentially eluted, each eluent having different pH's or salt concentrations: eluent having an acid pH is likely to be weakly positively charged whereas a fraction having a high pH is strongly positively charged.

A sample can be split up by isolating proteins that have a specific characteristic, e.g. are glycosylated. For example, a CSF sample can be split up by passing the sample over a lectin chromatography column (which has a high affinity for sugars). Glycosylated proteins will bind to the lectin column and non-glycosylated proteins will pass through the flow-through. Glycosylated proteins are then eluted from the lectin column with an eluent containing a sugar, e.g., N-acetyl-glucosamine and are available for further analysis.

Another way to determine biological sample composition is to eluate it through serial columns containing adsorbents directed against target proteins. Any suitable materials and methods can be used to perform sequential extraction of a sample. For example, we can use a series of spin columns containing different adsorbents, a multi-well coated with different adsorbents, a probe containing specific adsorbents adapted for use in a gas phase ion spectrometer (the probe is changed between two measurements). The advantage of performing sequential extraction on a gas phase ion spectrometer probe is that markers that bind to various adsorbents at every step of the extraction can be directly identified and analyzed.

Biomarkers in a sample can be also separated by high-resolution gel electrophoresis. This technique is particularly powerful when comparing related samples, such as healthy tissue versus disease samples (i.e. cerebral injury). For example, proteins that are more abundant in disease sample might represent novel drug targets or biomarkers. Comparative 2D-PAGE can also be used to look for proteins whose expression varies similarly under the same set of conditions (these may have related functions) and to identify proteins produced in response to drug therapy (these may be responsible for drug-related side effects).

The first step is to load the proteins onto the gel, which has a pH gradient from top to bottom. The polyacrylamide gel provides a supporting matrix through which proteins can migrate. This gel has a pH gradient from top to bottom—the top is more acidic than the bottom. A complex protein mixture is loaded in the middle of the left side, where the pH is neutral, and a voltage is applied across the gel. The proteins then migrate through the gel until they reach their isoelectric point (the point at which their charge is the same as the surrounding pH). This technique is called isoelectric focusing. The gel is then soaked in a denaturing solution (which causes the proteins to unfold) containing the detergent sodium dodecylsulphate (SDS). This molecule has a very strong negative charge and binds to all proteins, effectively making them all the same charge. A voltage is then applied across the gel from side to side with the anode (positive terminal) at the right. The proteins all move towards the anode, but smaller proteins move faster through the gel than larger ones, thus separating the proteins according to their size. Biomarkers in the two-dimensional array can be detected using any suitable methods known in the art. For example, biomarkers in a gel can be labelled or stained (e.g., Coomassie Blue or silver staining).

If gel electrophoresis generates spots that correspond to the molecular weight of one or more markers of the invention, the spot can be further analyzed by densitometry analysis or gas phase ion spectrometry using any suitable techniques, such as MALDI or SELDI.

The biomarkers may be subject to proteolysis before analysis. The fragments resulting from this digestion reflects the biomarkers identity, thereby enabling their analysis. This is particularly useful to distinguish different markers with similar molecular masses. Proteolysis is also useful for markers with high molecular weight that are less easily resolved by mass spectrometry than smaller markers. Proteases, such as trypsin, that cleaves the markers into a discrete number of fragments are particularly useful.

Biomarkers can also be modified to improve detection resolution. For instance, neuraminidase can be used to remove terminal sialic acid residues from glycoproteins, thus improving binding to an anionic adsorbent and improving detection resolution.

In another example, the biomarkers can be modified by the attachment of a tag of specific molecular weight. This tag will bind to a specific molecular marker, allowing further separation. Optionally, the identity of the modified biomarkers can be determined by matching their physical and chemical characteristics in a protein database (e.g., SwissProt).

High performance liquid chromatography (HPLC) can be used to separate a mixture of biomarkers in a sample based on their different physical properties, such as polarity, charge and size. HPLC instruments typically consist of a reservoir of mobile phase, a pump, an injector, a separation column, and a detector. Biomarkers in a sample are separated by injecting an aliquot of the sample onto the column. The mixture is eluted through the column at different rates due to differences in the partitioning behaviour between the mobile liquid and the stationary phases. A fraction that corresponds to the molecular weight and/or physical properties of one or more biomarkers is then collected. The fraction is analyzed by gas phase ion spectrometry to detect biomarkers.

The use of protein Biochip is of particular interest to determine the identity and level of expression of biomarkers present in biological sample. "Protein biochip" usually refers to the protein microarray, which has an orderly arrangement of many different proteins, such as antibodies, whose coordinates on the chip are known. Those proteins serve as capture agents for selected proteins in a sample. The captured proteins are made detectable either by labeling them directly with a fluorophore or, in the case of antibody chips, by adding a layer of labeled antibodies to make a sandwich. The position at which a protein binds reveals the type of antibody to which it binds and therefore its identity. The strength of the signal from that location indicates the protein level of expression. Antibody microarrays have the advantage of high throughput. The protein biochips can be provided by Packard BioScience Company (Meriden Conn.), Zyomyx (Hayward, Calif.) and Phylos (Lexington, Mass.).

To confirm the identity of the protein bound on a particular spot on the Biochips, it is necessary to perform further analysis.

Proteins captured on the surface of a protein bio chip can be detected by mass spectrometry, fluorescence, surface plasmon resonance, ellipsometry or atomic force microscopy. Mass spectrometry, is a useful method for detection of the biomarkers of this invention.

In laser desorption mass spectrometry, a substrate or a probe containing markers is introduced into an inlet system. The markers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

Matrix-assisted laser desorption/ionization mass spectrometry, or MALDI-MS, is a method of mass spectrometry that involves the use of an energy absorbing molecule, frequently called a matrix, for desorbing proteins intact from a probe surface. MALDI is described, for example, in U.S. Pat. No. 5,118,937 (Hillenkamp et al.) and U.S. Pat. No. 5,045,694 (Beavis and Chait). In MALDI-MS the sample is typically mixed with a matrix material and placed on the surface of an inert probe. Exemplary energy absorbing molecules include cinnamic acid derivatives, sinapinic acid ("SPA"), cyano hydroxy cinnamic acid ("CHCA") and dihydroxybenzoic acid. Other suitable energy absorbing molecules are known to those skilled in this art. The matrix dries, forming crystals that encapsulate the analyte molecules. Then the analyte molecules are detected by laser desorption/ionization mass spectrometry. MALDI-MS is useful for detecting the biomarkers of this invention if the complexity of a sample has been substantially reduced using the preparation methods described above.

Surface-enhanced laser desorption/ionization mass spectrometry, or SELDI-MS represents an improvement over MALDI for the fractionation and detection of biomolecules, such as proteins, in complex mixtures. SELDI is a method of mass spectrometry in which biomolecules, such as proteins, are captured on the surface of a protein biochip using capture reagents that are bound there. Typically, non-bound molecules are washed from the probe surface before interrogation. SELDI is described, for example, in: U.S. Pat. No. 5,719,060 (Hutchens and Yip, 1998,) U.S. Pat. No. 6,225,047 (Hutchens and Yip, 2001) and Weinberger et al., "Time-of-flight mass spectrometry," in Encyclopedia of Analytical Chemistry, R. A. Meyers, ed., pp 11915-11918 John Wiley & Sons Chichesher, 2000.

Markers on the substrate surface can be desorbed and ionized using gas phase ion spectrometry. In a typical mass spectrometer, a substrate or a probe comprising markers on its surface is introduced into an inlet system. The markers are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected and then information is translated into mass-to-charge ratios. Detection of the presence of markers or other substances will typically involve detection of signal intensity. This, in turn, can reflect the quantity and character of markers bound to the substrate.

Immunoassays

Biomarkers can be also detected and identified from biological fluids by immunoassay, using their properties to act as an antigen. The immunoassay implies: (a) to use antibodies that specifically binds to the markers; (b) to mix a sample with the antibody and (c) to detect the presence of antibody-marker complex in the sample.

Using the purified markers, antibodies that specifically bind to a marker can be prepared using any suitable methods known in the art. See, e.g., Coligan, Current Protocols in Immunology (1991); Harlow & Lane, Antibodies: A Laboratory Manual (1988); Goding, Monoclonal Antibodies: Principles and Practice (2d ed. 1986); and Kohler & Milstein, Nature 256:495-497 (1975). Such techniques include, but are not limited to, antibody preparation by selection of antibodies from libraries of recombinant antibodies in phage or similar vectors, as well as preparation of polyclonal and monoclonal antibodies by immunizing rabbits or mice (see, e.g., Huse et al., 1989; Ward et al., 1989).

Specific primary antibodies allow to quantify biomarkers in biological fluids using either an enzyme immune assay (EIA) such as enzyme-linked immunosorbent assay (ELISA), a radioimmune assay (RIA), a Western blot assay, or a slot blot assay (see, e.g., U.S. Pat. Nos. 4,366,241; 4,376,110; 4,517,288; and 4,837,168). These methods are also described in, e.g., Methods in Cell Biology: Antibodies in Cell Biology, volume 37 (Asai, ed. 1993); Basic and Clinical Immunology (Stites & Terr, eds., 7th ed. 1991). The detection and quantitation of biomarkers is described in detail in the Examples which follow.

Generally, the antibody that specifically binds the marker is added to the sample taken from a patient. Optionally, the antibody can be fixed to a solid support that will facilitate washing and subsequent isolation of the antibody-protein complex. Examples of solid supports include glass or plastic in the form of, e.g., a microtiter plate, a stick, a bead, or a microbead. Antibodies can also be attached to a probe substrate or "ProteinChip® arrays". A sample can be diluted in a suitable vehicle before being incubated with primary antibody. The mixture is washed and the antibody-marker complex can be detected with a specific reagent such as a secondary antibody labelled with magnetic beads (e.g., DYNABEADS™), fluorescent dyes, radiolabels, enzymes (e.g., horse radish peroxidase, alkaline phosphatase and others commonly used in an ELISA), and colorimetric labels such as colloidal gold or coloured glass or plastic beads.

Alternatively, the marker in the sample can be detected by a competition or inhibition assay wherein, for example, a two monoclonal antibodies directed against distinct epitopes are incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, biomarker identity, volume of solution, concentrations . . . . Usually the assays will be carried out at room temperature, although they can be conducted over a range of temperatures, such as 4° C. to 37° C.

Immunoassays are useful to determine level of expression of biomarkers in a test sample. This level of expression is determined by plotting absolute values to a standard curve (performed from a protein known to be present in a sample).

The analysis of the detection and quantification of biomarkers from tested samples, generate data that are displayed into various formats: 1) a "spectrum view or retentate map" where a standard spectral view depicts the quantity of biomarker reaching the detector at each particular molecular weight 2) a "peak map" where the peak height and mass information are visualized, yielding a cleaner image and enabling markers with nearly identical molecular weights to be more easily seen 3) a "gel view" where each mass from the peak view can be converted into a grey scale image based on the height of each peak, resulting in an appearance similar to bands on electrophoretic gels 4) a "3-D overlays" where several spectra can be overlaid to study subtle changes in relative peak heights 5) a "difference map view" where two or more spectra can be compared, conveniently highlighting unique markers and markers which are up- or down-regulated between samples 6) a "Spotfire Scatter Plot" where biomarkers are detected and plotted as a dot, one axis of the plot represents the apparent molecular mass of the markers detected and another axis represents the signal intensity of markers detected.

The methods exposed in this patent aim at detecting biomarkers in biological fluids from patients suffering of cerebral injuries. This process will lead to many applications. Quantification of biomarkers can then be used to precise the diagnosis cerebral injuries of any form and/or to monitor patient response to a treatment, and/or to identify compounds that modulate expression of these biomarkers in vivo or in vitro.

Further aspects and advantages of this invention will be disclosed in the following experimental section, which shall be considered as illustrative only.

EXAMPLES

A) Data Mining Process for Rational Selection of Ad-Relevant Biomarkers

A combinatorial approach is used for selection of potential AD biomarkers and their prioritization for validations studies, based on pathway mining of available experimental data covering results of functional cell biology studies, pan-genomic expression profiling experiments and genetic association studies (Herz & Beffert, 2000; Mattson, 2004; Ballatore et al., 2007; Li et al., 2008). This approach includes a few consecutive steps:

firstly, genes, functionally or genetically associated with AD, are grouped into relevantly small, previously described functional units, which represent minimal signalling transduction modules, these signalling transduction modules are further combined and maximally enlarged, basing on the analysis of publicly available functional studies, to construct AD-relevant pathways, large functional networks of interacting AD-relevant signalling pathways are defined, and individual biomarkers or rational combinations of biomarkers representing different functional networks are prioritized for functional annotation.

Thus, a potential biomarker, —either a protein itself or a product of any biochemical reaction catalyzed by this protein, —is selected and prioritized for validation studies, if it fits the following criteria:

participation in signalling pathway associated with onset and development of AD, participation in the functional network cogently represented by AD-associated pathways, facilitated detection in patient's samples.

Following data mining process, 214 genes have been selected as AD-biomarkers.

B) Identification of Biomarkers of the Invention

Genes, identified through our data analysis as associated with Alzheimer disease, constitute valuable biomarkers for characterizing patient condition and for allowing disease identification or subclassification.

An ELISA analysis of several human plasma samples is used for characterizing biomarkers of the invention Plasma Sample:

Blood is collected by standard methods from non diseased persons, persons at risk to develop AD, and AD patients who are undergoing or not a treatment. Samples are diluted in an equal volume of EDTA (conc) as an anticoagulant and then centrifuged (4° C., 1300RCF). Supernatants are aliquoted and frozen in liquid nitrogen. Samples are then stored at −80° C.

Elisa Analysis of Samples:

Conventional 96 well microplate sandwich ELISA is performed to quantify the average level of biomarkers of the invention in sets of plasma samples from diseased (control) or not diseased patients. This high throughput analysis is performed using an automated ELISA workstation.

Basically, procedure is almost the same as for standard sandwich ELISA:

PVC plates are first coated with capture antibodies diluted in PBS (1 µg per well, one night at 4° C.), after a wash step (in PBS), plates are then blocked with a 3% BSA containing PBS buffer overnight at 4° C.

Plates are then incubated with a titrated plasma/PBS solution overnight at 4° C.

After a wash step, monoclonal mouse detection antibodies are diluted in blocking buffer and incubated in plate wells for 2 hours.

After another wash step, a last blocking step is performed in 0.3% $H_2O_2$ methanol solution (to avoid residual peroxydase contamination from sample). After a PBS wash step, plates are incubated with HRP coupled, polyclonal anti mouse detection antibodies for two hours.

After a wash step, 0.5 mg/ml OPD solution in citrate phosphate buffer and supplemented with one thousandth of 30% $H_2O_2$ solution is applied for 10-15 min. An equal volume of stop solution (3M $H_2SO_4$) is added and $OD_{490}$ is then measured in each well.

Data Analysis from Proteomic Analysis.

Proteomic analysis (ELISA, above) of several samples of human plasma allows us to classify the 214 genes encoding circulating biomarkers identified from our data mining analysis, and optionally to determine which one or which set of proteins can constitute a specific signature for AD: A gene-by-gene analysis firstly applied on a training set of samples; this analysis is based on Random Forest (Díaz-Uriarte & Alvarez de Andrés, 2006) that ranks genes from the most discriminant ($gene_1$) between cases and controls to the least ($gene_{214}$).

From this analysis a set of 24 genes has been identified as the best biomarkers: Variation in corresponding protein level allows disease diagnostic with an accuracy of 60%. Remaining genes are grouped in two others lists: a significant variation in protein level of 51 genes is found in 50 to 60% of serums of diseased patients while between 40% and 50% of serums show a significant variation for the 139 remaining genes (Table 4).

TABLE 4

Circulant biomarkers classification

| gene | set |
|---|---|
| A2M | ++ |
| ABCC4 | + |
| ACC2 | + |
| ACHE | ++ |
| ACTN1 | + |
| ADAM12 | + |
| ADRA1A | + |
| AKAP13 | + |
| ALCAM | + |
| ALDH2 | ++ |
| ANXA1 | ++ |
| ANXA3 | + |
| APBA1 | +++ |
| APOA1 | ++ |
| ARHGEF11 | + |
| ARHGEF12 | + |
| ATF3 | + |
| ATG7 | +++ |
| ATM | + |
| ATP2A3 | ++ |
| ATP6V1C1 | + |
| ATR | + |
| BAP1 | + |
| BECN1 | +++ |
| BGLAP | + |
| BIN1 | + |
| BRIP1 | + |
| BSN | + |
| CACNA1D | + |
| CALCB | + |
| CASK | ++ |
| CASP8 | ++ |
| CD44 | +++ |
| CDC42BPB | + |
| CDH1 | ++ |
| CDH12 | + |
| CDH13 | + |
| CDH2 | +++ |
| CDH5 | ++ |
| CDKN1A | ++ |
| CHAT | ++ |
| CHEK1 | + |

TABLE 4-continued

Circulant biomarkers classification

| gene | set |
|---|---|
| CHL1 | + |
| CLTC | + |
| COL18A1 | +++ |
| COL3A3 | + |
| COPS7B | + |
| CSF1 | + |
| CSH1 | + |
| CSNK1A1 | + |
| CTNNA2 | + |
| CTNND2 | ++ |
| CUL1 | + |
| CYP11A1 | + |
| DAAM1 | + |
| DGKZ | + |
| DLG3 | + |
| DOCK2 | + |
| DOCK3 | ++ |
| EDN1 | ++ |
| EGF | + |
| EGFR | + |
| EPB41L2 | + |
| ERBB4 | +++ |
| ERC1 | + |
| F13A1 | ++ |
| F2 | + |
| F3 | +++ |
| FAS | + |
| FER1L3 | + |
| FES | + |
| FGF2 | ++ |
| FKBP1A | + |
| FLNA | +++ |
| FLNB | ++ |
| FSTL5 | + |
| FYN | +++ |
| GABRB2 | ++ |
| GFRA3 | + |
| GFRA4 | + |
| GH1 | + |
| GRIN2B | +++ |
| GRIP1 | + |
| GUCY2D | + |
| HGF | + |
| HIPK1 | + |
| HMBOX1 | + |
| HRG | + |
| HSP90B1 | + |
| HSPA5 | + |
| HYOU1 | + |
| IGF2 | + |
| IL16 | + |
| IL20 | +++ |
| IL6SI | + |
| IL8 | + |
| INS | + |
| IPPK | + |
| IQGAP1 | + |
| IQGAP2 | + |
| ITGA1 | ++ |
| ITGA9 | + |
| ITPR1 | +++ |
| JAK1 | + |
| LAMA1 | ++ |
| LAMA3 | ++ |
| LEP | + |
| LEPR | ++ |
| LETMD1 | + |
| LIFR | + |
| LRP1 | ++ |
| LRP2 | + |
| LRP6 | + |
| LRP8 | +++ |
| LTBP1 | + |
| MAD1L1 | + |
| MAML3 | + |
| MAP2 | ++ |

TABLE 4-continued

Circulant biomarkers classification

| gene | set |
|---|---|
| MMP2 | + |
| MMP3 | + |
| MMP9 | ++ |
| MSR1 | + |
| MTOR | +++ |
| MUC1 | + |
| MYO10 | + |
| NCAM1 | + |
| NCK1 | + |
| NFATC2 | ++ |
| NGF | + |
| NISCH | + |
| NOS1 | + |
| NOS3 | ++ |
| NOTCH2 | + |
| NOTCH3 | ++ |
| NPPA | + |
| NPPB | ++ |
| NPPC | +++ |
| NRIP1 | + |
| NRP1 | +++ |
| NTF3 | + |
| OPRM1 | + |
| PCAF | + |
| PCLO | + |
| PDE3A | + |
| PDE5A | + |
| PDGFA | ++ |
| PDGFB | ++ |
| PDGFC | +++ |
| PFKP | + |
| PIK3CA | + |
| PIK3CB | ++ |
| PLA2G2A | + |
| PLAT | + |
| PLAU | ++ |
| PLG | + |
| PLXDC2 | ++ |
| PLXNA2 | ++ |
| PRKG1 | ++ |
| PRL | + |
| PRLR | + |
| PRNP | ++ |
| PSAP | + |
| PSD3 | + |
| PTGS2 | + |
| PTK2 | ++ |
| PTK2B | + |
| PTPRF | + |
| PTPRG | + |
| PTPRM | + |
| RELN | + |
| RET | + |
| RIMS2 | + |
| ROBO1 | +++ |
| ROCK1 | + |
| RPS6KA1 | + |
| RPS6KA2 | + |
| RPS6KB1 | + |
| RYR2 | ++ |
| SCN9A | + |
| SEMA3E | +++ |
| SEMA5A | ++ |
| SERPINA5 | + |
| SERPINA6 | ++ |
| SERPINB2 | ++ |
| SERPINC1 | + |
| SERPIND1 | ++ |
| SERPINE1 | + |
| SERPINE2 | + |
| SNAP25 | + |
| SPP1 | + |
| SREBF2 | + |
| STAT3 | ++ |
| STAT5B | + |
| SV2B | + |
| TGFB1 | +++ |
| THBS1 | +++ |
| THBS2 | ++ |
| TIMP2 | + |
| TNF | ++ |
| TNF8F11 | + |
| TP53 | ++ |
| TRIO | + |
| TRPC4 | ++ |
| TSC1 | ++ |
| TSC2 | + |
| UBE3A | + |
| VCL | + |
| VEGFA | ++ |
| VEGFR1 | +++ |
| VTL2 | + |
| WASPIP | + |
| WWOX | +++ |
| XDH | + |
| ZFHX1B | + |

+++: preferred set of 24 biomarkers comprised in a set for AD diagnostic;
++: group of 51 biomarkers, a significant variation of which is found in 50% to 60% of samples of diseased patients;
+: group of 139 biomarkers, a significant variation of which is found in 40% to 50% of samples of diseased patients.

C) Other Methods of Identification and Quantitation, from Biological Samples, of Biomarkers of this Invention The methods exposed below aim at detecting biomarkers identified in this invention in biological fluids from patients suffering from cerebral injuries. Quantification of biomarkers can then be used to precise the diagnosis cerebral injuries of any kind and/or to monitor patient response to a treatment, and/or to identify compounds that modulate expression of these biomarkers in vivo or in vitro.

Biological samples are taken from healthy volunteers (controls), similar in age, gender, physical condition and from patients with cerebral injury. Comparisons of these biological samples allow detecting groups of biomarkers that characterizes patient condition and allow disease identification or subclassification.

Suitable detection and quantitation of biomarkers need to reduce the complexity of biological samples before performing analysis of biomarkers.

I) Sample Processing

Firstly, commercially available depletion chromatography columns are used to eliminate or reduce non relevant or over represented markers from the sample. Afterwards, routine techniques can be used to fractionate samples in fractions which contain biomarkers with similar properties binding properties or other physico-chemical characteristics. As an example, liquid chromatography techniques (size exclusion, ion exchange, heparin affinity . . . ) are well known in the art. In High performance liquid chromatography (HPLC), a high pressure is applied on the separating column once the sample is loaded. HPLC usually gives a better separation of biomarkers than common liquid chromatography.

a) Chromatography Techniques

Exclusion Chromatography

Exclusion chromatography might be used to split a sample according to the size of particles/molecules. High molecular weight proteins are eluted in the first elution fractions, the last ones containing a bigger percentage of small molecules (commercially available size exclusion columns can be Discovery® BIO Gel Filtration Columns or TSK-GEL Gel Filtration Columns, Sigma Aldrich)

Ion Exchange Chromatography

A sample is split up by ion exchange chromatography that allows separation of molecules according to their charge characteristics. Ion exchange resins are commercially disposable and allow fractionation of a sample in elution fractions ranked according to their pH. Anion exchange columns are used to separate negatively charged proteins, peptides as well as polynucleotides; cation exchange columns are used to separate proteins having a globally positive charge. (e.g. TSK-GEL® cation or anion-exchange Columns from TosoH Corp., Sigma Aldrich)

Bio Affinity Chromatography

Interaction properties of biomarkers, with proteins, metabolites, etc., can be used to separate them.

As an example heparin chromatography is used on the basis of affinity interaction with heparin and charge characteristics. Heparin, a sulfated mucopolysaccharide, will bind markers with positively charged moieties. Thus a sample is sequentially eluted, each eluent having different pH or salt concentrations: eluent having an acid pH is likely to be weakly positively charged whereas a fraction having a high pH is strongly positively charged.

A sample can be split up by isolating proteins that have a specific characteristic, e.g. posttranslational modification such as glycosylation. For example, a cerebrospinal fluid sample is loaded over a lectin chromatography column (which has a high affinity for sugars): Glycosylated proteins will bind to the lectin column and non-glycosylated proteins will pass through the flow-through. Glycosylated proteins are then eluted from the lectin column with an eluent containing a sugar, e.g., N-acetyl-glucosamine and are available for further analysis.

Serial Chromatography

An efficient way to split up a sample is to proceed to sequential extractions performing successive steps of chromatography which are based on different separation techniques. At every step retained or eluted markers can be analyzed.

b) Gel Electrophoresis Techniques

Biomarkers in a sample are separated according to their molecular mass performing a SDS PolyAcrylamide Gel Electrophoresis (known as SDS-PAGE). Two dimensional gel electrophoresis (2D-PAGE) is a two steps electrophoresis that can be used to analyze mixture of proteins:

The first step is isoelectric focusing. Proteins are loaded onto a gel that has a pH gradient from top to bottom. The proteins then migrate through the gel until they reach their isoelectric point. The second step is a conventional SDS PAGE: the proteins are then separated according to their Molecular Mass. Biomarkers so separated in the two-dimensional gel can be detected using any suitable methods which are well known in the art. For example, biomarkers in a gel can be labelled or stained (e.g., Coomassie Blue or silver staining).

Comparison of a reference 2D gel to a 2D gel corresponding to a sample from a diseased patient allows identification of present or absent biomarkers but also determination of the relative expression ratio of biomarkers of interest: Biomarkers spots can be further analyzed by densitometry analysis or gas phase ion spectrometry using any suitable techniques, such as MALDI (cf II).

II) Identification and Quantitative Analysis of Biomarkers a) Biochips

Protein Microarrays

The use of protein Biochip is of particular interest to determine the identity and the expression of a set of biomarkers present in biological sample.

Biomarkers of a biological sample are first captured by capture agents plotted on the microarray surface. Captures agents can be nonspecific: They use the same principle that chromatography techniques based on the use of physic chemical properties of molecules (pH, charge, hydrophobicity etc. . . . ). Spectrometry is then used to identify biomarkers that have been retained by captures agents. This technique, called Seldi MS, is useful for high-throughput analysis of a complex sample, providing expression levels of a large set of biomarkers and identifying relevant biomarker(s) in a mixture of molecules.

Capture agents can also be specific of known biomarkers. Antibodies, prey proteins, aptamers . . . could be used to generate "Protein biochip" dedicated to the detection and/or quantitation of biomarkers one is searching for.

Antibody microarrays technology derives from sandwich, capture or competitive capture immunoassays (cf below). Antibodies are orderly linked to microarray surface. The sample, optionally conditioned or partially purified (cf I), is incubated with the microarray. The mixture is then washed and the antibody-biomarker complex is detected with a specific reagent such as a secondary antibody labelled with magnetic beads (e.g., DYNABEADS™), fluorescent dyes, radiolabels, enzymes (e.g., horse radish peroxide, alkaline phosphatase and others commonly used in an ELISA), and colorimetric labels such as colloidal gold or coloured glass or plastic beads.

Protein biochips are commercially available for seeking specific proteins families or cellular pathways (e.g., BioRay (Norcross, Ga.); Sigma Aldrich's panorama microarrays) or can be designed upon demand (e.g., Primorigen biosciences (Madison, Wis.); Arrayit Corporation (Sunnyvale, Calif.); MicroBioChips Sas (Paris, France)).

DNA Chips

DNA chips are used for two applications.

Firstly, they allow quantification of gene expression at the RNA level, also called gene expression profiling. Gene expression profiling consists in measuring from cDNA the levels of expression of thousands of genes. Genes whose expression is affected by a pathology or a treatment can thus be identified and used as biomarkers (King & Sinha, 2001, Ghanem et al., 1992). DNA chips can be used as a complementary approach for detecting variability in expression of potential biomarkers.

DNA chips can also be used to detect polymorphisms, for instance single nucleotide polymorphism (SNP) or microdeletions, allowing identification of disease associated genetic markers.

The genome can thus be screened for the presence of polymorphisms associated to a disease or a treatment response, becoming useful biomarkers. (Anderson et al., 2006, Shi, 2001; Chial, 2008).

b) Mass Spectrometry

Mass spectrometry (MS) can be used to identify a purified biomarker or biomarkers present in a fraction of sample obtained during sample processing. Protein biomarkers may be subject to proteolysis before analysis. The fragments resulting from this digestion reflects the biomarkers identity, thereby enabling their analysis. This is particularly useful to distinguish different markers with similar molecular masses (purified from a SDS PAGE for example) or present in a same elution fraction. Proteolysis is also useful for markers with high molecular weight that are less easily resolved by mass spectrometry than smaller markers. Proteases, as trypsin, that cleaves the markers into a discrete number of fragments are commercially available.

Post translational modified protein biomarkers may need to be modified to improve detection resolution. For instance, neuraminidase can be used to remove terminal sialic acid residues from glycoproteins, thus improving binding to an anionic adsorbent and improving detection resolution.

Several improvements in Mass Spectrometry techniques can be used for identifying biomarkers present in a sample: Tandem Mass spectrometery (MS-MS), electron spray ionization, Laser desorption mass spectrometry, Matrix-Assisted Laser Desorption/Ionization Mass Spectrometry (MALDI-MS), MALDI-TOF-MS.

These techniques are useful for detecting the biomarkers of this invention once the complexity of a sample has been substantially reduced using the preparation methods described above.

Surface-enhanced laser desorption/ionization mass spectrometry (SELDI-MS) represents an improvement over MALDI for the fractionation and detection of biomolecules present in a weak quantity in complex mixtures. In SELDI-MS technique, biomolecules, such as proteins, are captured on the surface of a protein biochip using capture reagents that are bound on the biochip. As in chromatography techniques cited above, capture reagents are used to reduce complexity of a biological sample, using physico chemical properties of biomolecules (reviewed in De Bock M, 2010; U.S. Pat. No. 6,528,320 (Hutchens and Yip)).

c) Immunoassays

Biomarkers can be also detected, identified and quantified from biological fluids by immunoassays, using their properties to act as an antigen. Antibodies specific to the biomarkers of interest can be either produced using methods currently used or are commercially available (See, e.g., Coligan, Current Protocols in Immunology (1991); Harlow & Lane, Antibodies: A Laboratory Manual (1988)). Expression level of biomarkers is determined by plotting absolute values to a standard curve (performed from a protein known to be present in a sample). Such immunoassays can be for example: radioimmunoassays, ELISA (enzyme linked immunosorbent assay), "sandwich" immunoassays, immunoprecipitation assays, precipitin reactions, gel diffusion precipitin reactions, immunodiffusion assays, fluorescent immunoassays and the like. Such assays are routine and well known in the art (See, e.g., Coligan, Current Protocols in Immunology (1991); Harlow & Lane, Antibodies: A Laboratory Manual (1988)).

MS is useful for detecting and quantify any kind of biomarkers, proteins, but also carbohydrates, lipids or biomolecule of any kind: MS can be used to perform metabolomic analyses (Boccard J. et al, 2010). Results with metabolomic or proteomic studies performed using, for example, MS or protein chips can be improved using biomarkers identified from genomic data obtained with DNA arrays (as well as RNA expression level, or polymorphism data).

Results:

Identification of sets of AD-biomarkers.

Numerous combinations of AD-biomarkers have been identified by inventors using chromatography techniques and protein microarrays as described above. The most preferred sets of AD-biomarkers contain biomarkers listed in Table 4.

D) Methods of Detection of the Presence or Risk of AD in a Human Plasma Sample Using Biomarkers of the Invention I) AD Diagnostic Using ELISA Assay Blood samples are collected by standard methods from persons wishing to evaluate the risk of AD or the presence of AD. Control sample is made from the mix of several blood samples from healthy volunteers. Samples are diluted in an equal volume of EDTA (conc) as an anticoagulant and then centrifuged (4° C., 1300RCF). Supernatants are aliquoted and frozen in liquid nitrogen. Samples are then stored at −80° C.

Elisa protocol is performed according to the procedure described above in part B). PVC plates are first coated with antibodies for each of 24 preferred biomarkers listed in Table 4. These antibodies are diluted in PBS (1 µg per well, one night at 4° C.), after a wash step (in PBS), plates are then blocked with a 3% BSA containing PBS buffer overnight at 4° C.

Conventional 96 well microplate sandwich ELISA is performed to quantify the level of biomarkers of the invention in plasma samples from tested patients. This high throughput analysis is performed using an automated ELISA workstation. Plates are then incubated with a titrated plasma/PBS solution overnight at 4° C.

After a wash step, monoclonal mouse detection antibodies are diluted in blocking buffer and incubated in plate wells for 2 hours. After another wash step, a last blocking step is performed in 0.3% $H_2O_2$ methanol solution (to avoid residual peroxydase contamination from sample). After a PBS wash step, plates are incubated with HRP coupled, polyclonal anti mouse detection antibodies for two hours.

After a wash step, 0.5 mg/ml OPD solution in citrate phosphate buffer and supplemented with one thousandth of 30% $H_2O_2$ solution is applied for 10-15 min. An equal volume of stop solution (3M $H_2SO_4$) is added and antibody/protein binding is evaluated by measure of $OD_{490}$ in each well for each of 24 biomarker proteins.

Finally, the risk of AD or the presence of AD is determined by evaluation of the binding profile of biomarker proteins to capture antibodies (i.e., number and identity of biomarkers for which a significant difference in protein level is observed between test and control samples) and by determining if the variation in corresponding protein level is in accordance with level variations that have been observed during the step of identification of the biomarkers.

II) AD Diagnostic Using DNA Microarrays

Classical protocol is used for detection DNA sequences with DNA microarray. Blood samples from patients wishing to be diagnosed for the risk of AD or the presence of AD are collected in PAXgene blood RNA tubes (Qiagen). Blood samples drawn from healthy patients are collected, mixed to constitute reference sample which is treated as blood sample to be diagnosed.

Total RNA is extracted from these samples using the PAXgene Blood RNA Kit (Qiagen) according to the manufacturer's recommendations.

Total RNA is quantified, and 5 µg to 10 µg of RNA is reverse transcribed. ds cDNA is synthesized. In vitro transcription is then performed using aa dUTP, and aRNAs are indirectly labelled with Cy-dye esters.

DNA chips containing DNA probes complementary to the nucleotide sequence coding for each of 24 biomarkers are used for detection of the presence or the risk of AD. Each slide is hybridized labelled aRNAs from sample to be diagnosed vs labelled aRNAs from reference sample. Dye swap hybridizations are performed. Probe-target hybridization is detected and quantified and the compared gene expression profiling is evaluated. The presence or the risk of AD is estimated as a function of the number of biomarkers, expression of which is altered comparing to its expression in healthy patient.

REFERENCES

Acevedo L M, Barillas S, et al. Semaphorin 3A suppresses VEGF-mediated angiogenesis yet acts as a vascular permeability factor. Blood 2008; 111 (5): 2674-2680.

Anderson J E, Hansen L L, Mooren F C, Post M, Hug H, Zuse A, Los M. Methods and biomarkers for the diagnosis and prognosis of cancer and other diseases: towards personalized medicine. Drug Resist Updat. 2006; 9(4-5): 198-210.

Ausubel eds 1994, Current Protocols in Molecular Biology, Vol. 1, John Wiley & Sons, Inc., New York, which is incorporated by reference herein in its entirety Ballatore C, Lee V M et al. Tau-mediated neurodegeneration in Alzheimer's disease and related disorders. Nature Reviews Neurosci 2007; 8: 663-672.

Ballatore C., Lee V. M., et al. (2007). Tau-mediated neurodegeneration in Alzheimer's disease and related disorders. Nat Rev Neurosci. 8(9): 663-72.

Blennow K, Davidsson P, Wallin A, Ekman R. Chromogranin A in cerebrospinal fluid: a biochemical marker for synaptic degeneration in Alzheimer's disease? Dementia. 1995; 6(6):306-11.

Boccard J, Veuthey J L, Rudaz S. Knowledge discovery in metabolomics: an overview of MS data handling. J Sep Sci. 2010; 33(3):290-304.

Brose K, Tessier-Lavigne M. Slit proteins: key regulators of axon guidance, axonal branching, and cell migration. Curr Opin Neurobiol. 2000; 10(1): 95-102.

Burbach G J, Hellweg R, Haas C A, Del Turco D, Deicke U, Abramowski D, Jucker M, Staufenbiel M, Deller T. Induction of brain-derived neurotrophic factor in plaque-associated glial cells of aged APP23 transgenic mice. J. Neurosci. 2004; 24(10):2421-30.

Cao G, Savani R C et al. Involvement of endothelial CD44 during in vivo angiogenesis. Am J Pathol. 2006; 169(1): 325-336.

Cao R, Brakenhielm E et al. Leptin induces vascular permeability and synergistically stimulates angiogenesis with FGF-2 and VEGF. Proc Natl Acad Sci USA. 2001; 98(11): 6390-6395.

Chial, H. (2008) Rare genetic disorders: Learning about genetic disease through gene mapping, SNPs, and microarray data. Nature Education 1(1)

Citron M. (2004). Strategies for disease modification in Alzheimer's disease. Nat Rev Neurosci. 5(9): 677-85.

Davidsson P, Westman-Brinkmalm A, Nilsson C L, Lindbjer M, Paulson L, Andreasen N, Sjögren M, Blennow K. Proteome analysis of cerebrospinal fluid proteins in Alzheimer patients. Neuroreport. 2002 16; 13 (5): 611-5.

De Bock M, de Seny D, Meuwis M A, Chapelle J P, Louis E, Malaise M, Merville M P, Fillet M. Challenges for biomarker discovery in body fluids using SELDI-TOF-MS. J Biomed Biotechnol. 2010; 2010

Díaz-Uriarte R. and Alvarez de Andrés S. BMC Bioinformatics. 2006; 7: 3

Elovaara I. Proteins in serum and cerebrospinal fluid in demented patients with Down's syndrome. Acta Neurol Scand. 1984; 69(5):302-5.

English D, Kovala A T et al. Induction of endothelial cell chemotaxis by sphingosine 1-phosphate and stabilization of endothelial monolayer barrier function by lysophosphatidic acid, potential mediators of hematopoietic angiogenesis. J Hematother Stem Cell Res. 1999; 8(6):627-634.

Fahnestock M, Garzon D, Holsinger R M, Michalski B. Neurotrophic factors and Alzheimer's disease: are we focusing on the wrong molecule? J Neural Transm Suppl. 2002; (62):241-52

Ferrara N, Gerber H et al. The biology of VEGF and its receptors. Nat. Med. 2003; 9(6): 669-676.

Fiedler U, Krissl T et al. Angiopoietin-1 and angiopoietin-2 share the same binding domains in the Tie-2 receptor involving the first Ig-like loop and the epidermal growth factor-like repeats. J Biol Chem. 2003; 278(3):1721-1727.

Fukushima N, Weiner J A et al. Lysophosphatidic acid influences the morphology and motility of young, postmitotic cortical neurons. Mol Cell Neurosci. 2002; 20(2): 271-282.

Ge G, Fernández C A et al. Bone morphogenetic protein 1 processes prolactin to a 17-kDa antiangiogenic factor". Proc Natl Acad Sci USA. 2007; 104(24):10010-10015.

Guan K L, Rao Y. Signalling mechanisms mediating neuronal responses to guidance cues. Nat Rev Neurosci. 2003; 4(12): 941-956.

Ghanem N, Fanen P, Martin J, Conteville P, Yahia-Cherif Z, Vidaud M, Goossens M. Exhaustive screening of exon 10 CFTR gene mutations and polymorphisms by denaturing gradient gel electrophoresis: applications to genetic counselling in cystic fibrosis. Mol Cell Probes. 1992; 6(1):27-31.

Harigaya Y, Shoji M, Nakamura T, Matsubara E, Hosoda K, Hirai S. Alpha 1-antichymotrypsin level in cerebrospinal fluid is closely associated with late onset Alzheimer's disease. Intern Med. 1995; 34(6):481-4.

Harrington M G, Aebersold R, Martin B M, Merril C R, Hood L. Identification of a brain-specific human cerebrospinal fluid glycoprotein, beta-trace protein. Appl Theor Electrophor. 1993; 3(5):229-34.

Herz J, Beffert U. Apolipoprotein e receptors: linking brain development and Alzheimer's disease. Nature Reviews Neurosci 2000; 1: 51-58.

Hiraoka A, Arato T, Tominaga I, Eguchi N, Oda H, Urade Y. Sodium dodecyl sulfate-capillary gel electrophoretic analysis of molecular mass microheterogeneity of beta-trace protein in cerebrospinal fluid from patients with central nervous system diseases. J Chromatogr A. 1998; 802(1):143-8.

Hiraoka A, Seiki K, Oda H, Eguchi N, Urade Y, Tominaga I, Baba K. Charge microheterogeneity of the beta-trace proteins (lipocalin-type prostaglandin D synthase) in the cerebrospinal fluid of patients with neurological disorders analyzed by capillary isoelectrofocusing. Electrophoresis. 2001; 22(16):3433-7.

Hoekman K, Van Nieuwkoop J A, Willemze R. The significance of beta-2 microglobulin in clinical medicine. Neth J Med. 1985; 28(12):551-7.

Hong K, Hinck L et al. A ligand-gated association between cytoplasmic domains of UNC5 and DCC family receptors converts netrin-induced growth cone attraction to repulsion. Cell 1999; 97:927-941.

Hsieh M Y, Chen W Y et al. Interleukin-20 promotes angiogenesis in a direct and indirect manner. Genes Immun. 2006; 7(3): 234-242.

Huse W D, Sastry L, Iverson S A, Kang A S, Alting-Mees M, Burton D R, Benkovic S J, Lerner R A. Generation of a large combinatorial library of the immunoglobulin repertoire in phage lambda. Science. 1989; 246(4935):1275-81.

Iqbal K, Alonso A C, Gong C X, Khatoon S, Pei J J, Wang J Z, Grundke-Iqbal I. Mechanisms of neurofibrillary degeneration and the formation of neurofibrillary tangles. J Neural Transm Suppl. 1998; 53:169-80.

Kawashima M, Suzuki S O, Yamashima T, Fukui M, Iwaki T. Prostaglandin D synthase (beta-trace) in meningeal hemangiopericytoma. Mod Pathol. 2001; 14(3):197-201.

King H C, Sinha A A. Gene expression profile analysis by DNA microarrays: promise and pitfalls. JAMA. 2001; 286(18):2280-8.

Köhler G, Milstein C. Continuous cultures of fused cells secreting antibody of predefined specificity. Nature. 1975 7; 256(5517):495-7.

Kudo T, Iqbal K, Ravid R, Swaab D F, Grundke-Iqbal I. Alzheimer disease: correlation of cerebro-spinal fluid and brain ubiquitin levels. Brain Res. 1994; 639(1):1-7.

Leeuwen F N, Kain H E et al. The guanine nucleotide exchange factor Tiam1 affects neuronal morphology; opposing roles for the small GTPases Rac and Rho. J. Cell Biol. 1997; 139(3):797-807.

Levy E, Sastre M, Kumar A, Gallo G, Piccardo P, Ghetti B, Tagliavini F. Codeposition of cystatin C with amyloid-beta protein in the brain of Alzheimer disease patients. J Neuropathol Exp Neurol. 2001; 60(1):94-104.

Li H, Wetten S et al., Candidate Single-Nucleotide Polymorphisms From a Genomewide Association Study of Alzheimer Disease. Arch Neurol. 2008; 65(1): 45-53.

Li X L, Aou S, Oomura Y, Hori N, Fukunaga K, Hori T. Impairment of long-term potentiation and spatial memory in leptin receptor-deficient rodents. Neuroscience 2002; 113(3):607-15.

Mase M, Yamada K, Iwata A, Matsumoto T, Seiki K, Oda H, Urade Y. Acute and transient increase of lipocalin-type prostaglandin D synthase (beta-trace) level in cerebrospinal fluid of patients with aneurysmal subarachnoid hemorrhage. Neurosci Lett. 1999; 270(3):188-90.

Mase M, Yamada K, Shimazu N, Seiki K, Oda H, Nakau H, Inui T, Li W, Eguchi N, Urade Y. Lipocalin-type prostaglandin D synthase (beta-trace) in cerebrospinal fluid: a useful marker for the diagnosis of normal pressure hydrocephalus. Neurosci Res. 2003; 47(4):455-9.

Masliah E, Mallory M, Alford M, Deteresa R, Saitoh T. PDGF is associated with neuronal and glial alterations of Alzheimer's disease. Neurobiol Aging. 1995; 16(4):549-56.

Matsubara E, Hirai S, Amari M, Shoji M, Yamaguchi H, Okamoto K, Ishiguro K, Harigaya Y, Wakabayashi K. Alpha 1-antichymotrypsin as a possible biochemical marker for Alzheimer-type dementia. Ann Neurol. 1990; 28(4):561-7.

Mattson M P. Pathways towards and away from Alzheimer's disease. Nature 2004; 430: 631-639.

McKhann G, Drachman D, Folstein M, Katzman R, Price D, Stadlan E M, Clinical diagnosis of Alzheimer's disease: report of the NINCDS-ADRDA Work Group under the auspices of Department of Health and Human Services Task Force on Alzheimer's Disease. Neurology. 1984; 34(7):939-44.

Melegos D N, Freedman M S, Diamandis E P. Prostaglandin D synthase concentration in cerebrospinal fluid and serum of patients with neurological disorders. Prostaglandins. 1997; 54(1):463-74.

Merched A, Serot J M, Visvikis S, Aguillon D, Faure G, Siest G. Apolipoprotein E, transthyretin and actin in the CSF of Alzheimer's patients: relation with the senile plaques and cytoskeleton biochemistry. FEBS Lett. 1998; 425(2):225-8.

Moriya J, Minamino T et al. Semaphorin 3E/Plexin D1 as a Novel Target for Therapeutic Angiogenesis. Circulation 2007; 116(II):231.

Nguyen A, Cai H. Netrin-1 induces angiogenesis via a DCC-dependent ERK1/2-eNOS feed-forward mechanism. PNAS USA 2006; 103(17): 6530-6535.

Noren N K, Pasquale E B. Eph receptor-ephrin bidirectional signals that target Ras and Rho proteins. Cell Signal. 2004; 16(6):655-666.

Park S Y, Jeong K J et al. Hypoxia enhances LPA-induced HIF-1alpha and VEGF expression: their inhibition by resveratrol". Cancer Lett. 2007; 258(1):63-69.

Petersen R C, Smith G E, Waring S C, Ivnik R J, Tangalos E G, Kokmen E. Mild cognitive impairment: clinical characterization and outcome. Arch Neurol. 1999; 56(3): 303-8. Erratum in: Arch Neurol 1999; 56(6):760.

Potter H, Wefes I M, Nilsson L N. The inflammation-induced pathological chaperones ACT and apo-E are necessary catalysts of Alzheimer amyloid formation. Neurobiol Aging. 2001; 22(6):923-30.

Power D A, Noel J, Collins R, O'Neill D. Circulating Leptin Levels and Weight Loss in Alzheimer's Disease Patients. Dement Geriatr Cogn Disord 2001; 12:167-170.

Riisøen H. Reduced prealbumin (transthyretin) in CSF of severely demented patients with Alzheimer's disease. Acta Neurol Scand. 1988; 78(6):455-9.

Sanna V, Di Giacomo A, La Cava A, Lechler R I, Fontana S, Zappacosta S, Matarese G. Leptin surge precedes onset of autoimmune encephalomyelitis and correlates with development of pathogenic T cell responses. J Clin Invest. 2003; 111(2):183-5.

Serot J M, Christmann D, Dubost T, Couturier M. Cerebrospinal fluid transthyretin: aging and late onset Alzheimer's disease. J Neurol Neurosurg Psychiatry. 1997; 63(4): 506-8.

Shi M. Enabling large-scale pharmacogenetic studies by high-throughput mutation detection and genotyping technologies. Clin Chem. 2001; 47(2):164-72.

Skoog I, Wallin A, Fredman P, Hesse C, Aevarsson O, Karlsson I, Gottfries C G, Blennow K. A population study on blood-brain barrier function in 85-year-olds: relation to Alzheimer's disease and vascular dementia. Neurology. 1998; 50(4):966-71.

Sottile J. Regulation of angiogenesis by extracellular matrix. Biochim Biophys Acta. 2004; 1654(1): 13-22.

Stein E, Tessier-Lavigne M. Hierarchical organization of guidance receptors: silencing of netrin attraction by slit through a Robo/DCC receptor complex. Science 2001; 291:1928-1938.

Suh Y. H. and Checker F. (2002). Amyloid precursor protein, presenilins, and alpha-synuclein: molecular pathogenesis and pharmacological applications in Alzheimer's disease. Pharmacol Rev. 54(3): 469-525.

Tsuzuki K, Fukatsu R, Yamaguchi H, Tateno M, Imai K, Fujii N, Yamauchi T. Transthyretin binds amyloid beta peptides, Abeta1-42 and Abeta1-40 to form complex in the autopsied human kidney—possible role of transthyretin for abeta sequestration. Neurosci Lett. 2000; 281(2-3):171-4.

Wang G P, Iqbal K, Bucht G, Winblad B, Wisniewski H M, Grundke-Iqbal I. Alzheimer's disease: paired helical filament immunoreactivity in cerebrospinal fluid. Acta Neuropathol. 1991; 82(1):6-12.

Ward E S, Güssow D, Griffiths A D, Jones P T, Winter G. Binding activities of a repertoire of single immunoglobulin variable domains secreted from *Escherichia coli*. Nature. 1989; 341(6242):544-6. West D C, Hampson I N et al. Angiogenesis induced by degradation products of hyaluronic acid. Science 1985; 228(4705): 1324-1326.

Winning R S, Ward E K et al. EphA4 catalytic activity causes inhibition of RhoA GTPase in *Xenopus laevis* embryos. Differentiation 2002; 70(1):46-55.

The invention claimed is:

1. A method for detecting the amount of each biomarker in a set of biomarkers in a sample from a mammal and optionally, in a control sample, said method comprising contacting said set of biomarkers with antibody specific to said each biomarker in said set of biomarkers and detecting the binding of antibodies specific to each biomarker in said set of biomarkers, wherein said set of biomarkers comprises 24 proteins encoded by the following 24 genes: APBA1, ATG7, BECN1, CD44, CDH2, COL18A1, ERBB4, F3, FLNA, FYN, GRIN2B, IL20, ITPR1, LRP8, MTOR, NPPC, NRP1, PDGFC, ROBO1, SEMA3E, TGFB1, THBS1, VEGFR1 and WWOX.

2. The method of claim 1, wherein the set of biomarkers further comprises at least one protein encoded by a gene selected from: A2M, ACHE, ALDH2, ANXA1, APOA1, ATP2A3, CASK, CASP8, CDH1, CDH5, CDKN1A, CHAT, CTNND2, DOCK3, EDN1, F13A1, FGF2, FLNB, GABRB2, ITGA1, LAMA1, LAMA3, LEPR, LRP1, MAP2, MMP9, NFATC2, NOS3, NOTCH3, NPPB, PDGFA, PDGFB, PIK3CB, PLAU, PLXDC2, PLXNA2, PRKG1, PRNP, PTK2, RYR2, SEMA5A, SERPINA6, SERPINB2, SERPIND1, STAT3, THBS2, TNF, TP53, TRPC4, TSC1 or VEGFA.

3. The method of claim 2, wherein at least one further biomarker is selected from disease associated SNP, a protein, RNA, metabolite, lipid or glucid.

4. The method of claim 3, wherein the at least one further biomarker is selected from metabolites of the:
cholesterol metabolic pathway; and/or
folate metabolic pathway; and/or
phosphatidic acid metabolic pathway; and/or
sphingosine metabolic pathway; and/or
terpenoid metabolic pathway.

5. The method of claim 3, wherein the at least one further biomarker is a SNP or a combination of SNPs for the genes selected from: APBA1, ATG7, BECN1, CD44, CDH2, COL18A1, ERBB4, F3, FLNA, FYN, GRIN2B, 1L20, ITPR1, LRP8, MTOR, NPPC, NRP1, PDGFC, ROBO1, SEMA3E, TGFB1, THBS1, VEGFR1 or WWOX, or for other genes involved in synapse biology, angiogenesis or cellular stress response.

6. The method of claim 1, wherein the set of biomarkers further comprises at least one protein encoded by a gene selected from: ABCC4, ACC2, ACTN1, ADAM12, ADRA1A, AKAP13, ALCAM, ANXA3, ARHGEF11, ARHGEF12, ATF3, ATM, ATP6V1C1, ATR, BAP1, BGLAP, BIN1, BRIP1, BSN, CACNA1D, CALCB, CDC42BPB, CDH12, CDH13, CHEK1, CHL1, CLTC, COL3A1, COPS7B, CSF1, CSH1, CSNK1A1, CTNNA2, CUL1, CYP11A1, DAAM1, DGKZ, DLG3, DOCK2, EGF, EGFR, EPB41L2, ERC1, F2, FAS, FER1L3, FES, FKBP1A, FSTL5, GFRA3, GFRA4, GH1, GRIP1, GUCY2D, HGF, HIPK1, HMBOX1, HRG, HSP90B1, HSPA5, HYOU1, IGF2, IL16, IL6ST, IL8, INS, IPPK, IQGAP1, IQGAP2, ITGA9, JAK1, LEP, LETMD1, LIFR, LRP2, LRP6, LTBP1, MAD1L1, MAML3, MMP2, MMP3, MSR1, MUC1, MYO10, NCAM1, NCK1, NGF, NISCH, NOS1, NOTCH2, NPPA, NRIP1, NTF3, OPRM1, PCAF, PCLO, PDE3A, PDE5A, PFKP, PIK3CA, PLA2G2A, PLAT, PLG, PRL, PRLR, PSAP, PSD3, PTGS2, PTK2B, PTPRF, PTPRG, PTPRM, RELN, RET, RIMS2, ROCK1, RPS6KA1, RPS6KA2, RPS6KB1, SCN9A, SERPINA5, SERPINC1, SERPINE1, SERPINE2, SNAP25, SPP1, SREBF2, STAT5B, SV2B, TIMP2, TNFSF11, TRIO, TSC2, UBE3A, VCL, VIL2, WASPIP, XDH or ZFHX1B.

7. The method of claim 1, wherein the sample is selected from blood, serum and plasma.

8. The method of claim 1, wherein the quantification of the amount of said proteins is carried out using a protein biochip.

9. The method of claim 8, wherein said method comprises contacting a plasma sample from the mammal and optionally, the control sample, with the protein biochip, said protein biochip comprising antibodies specific for APBA1, ATG7, BECN1, CD44, CDH2, COL18A1, ERBB4, F3, FLNA, FYN, GRIN2B, IL20, ITPR1, LRP8, MTOR, NPPC, NRP1, PDGFC, ROBO1, SEMA3E, TGFB1, THBS1, VEGFR1 and WWOX and the binding of said target biomarker to its specific antibody to form an antibody-biomarker complex and detecting antibody-biomarker complexes formed during said contacting with labelled secondary antibodies specific for APBA1, ATG7, BECN1, CD44, CDH2, COL18A1, ERBB4, F3, FLNA, FYN, GRIN2B, 1L20, ITPR1, LRP8, MTOR, NPPC, NRP1, PDGFC, ROBO1, SEMA3E, TGFB1, THBS1, VEGFR1 and WWOX.

10. A method of detecting a combination of biomarkers, the method comprising contacting a plasma sample from a subject, and optionally, a control sample, with a protein biochip comprising antibodies specific for APBA1, ATG7, BECN1, CD44, CDH2, COL18A1, ERBB4, F3, FLNA, FYN, GRIN2B, IL20, ITPR1, LRP8, MTOR, NPPC, NRP1, PDGFC, ROBO1, SEMA3E, TGFB1, THBS1, VEGFR1 and WWOX and detecting antibody-biomarker complexes formed during said contacting with labelled secondary antibodies specific for APBA1, ATG7, BECN1, CD44, CDH2, COL18A1, ERBB4, F3, FLNA, FYN, GRIN2B, 1L20, ITPR1, LRP8, MTOR, NPPC, NRP1, PDGFC, ROBO1, SEMA3E, TGFB1, THBS1, VEGFR1 and WWOX.

* * * * *

UNITED STATES PATENT AND TRADEMARK OFFICE
CERTIFICATE OF CORRECTION

PATENT NO. : 9,493,834 B2                       Page 1 of 1
APPLICATION NO. : 13/387174
DATED : November 15, 2016
INVENTOR(S) : Cohen et al.

It is certified that error appears in the above-identified patent and that said Letters Patent is hereby corrected as shown below:

In the Specification

Column 21,
Line 6, "RPS6 KB1," should read --RPS6KB1,--.
Line 62, "VAMPS," should read --VAMP5,--.

Column 22,
Line 55, "GNAI2, GNAI3, GNAI1," should read --GNA12, GNA13, GNAI1,--.
Line 64, "SILL," should read --SIL1,--.

Column 32,
Line 48, "Elisa" should read --ELISA--.

Column 34,
Line 8, "COL3A3" should read --COL3A1--.

Signed and Sealed this
Eleventh Day of April, 2017

Michelle K. Lee
*Director of the United States Patent and Trademark Office*